US010035841B2

(12) United States Patent
Clavijo et al.

(10) Patent No.: US 10,035,841 B2
(45) Date of Patent: Jul. 31, 2018

(54) MONOCLONAL ANTIBODY AGAINST NOVEL EPITOPES OF FOOT-AND-MOUTH DISEASE VIRUS PROTEIN 3ABC AND USES THEREOF

(71) Applicants: Alfonso Clavijo, Rio de Janeiro (BR); Aida Elizabeth Rieder, Westbrook, CT (US); Abu Sayed, East Lyme, CT (US); Mangkey A. Bounpheng, Austin, TX (US); Thomas G. Burrage, Guilford, CT (US); Brooke A. Dancho, Athens, GA (US); Sabena Uddowla Blakeney, Lanham, MD (US)

(72) Inventors: Alfonso Clavijo, Rio de Janeiro (BR); Aida Elizabeth Rieder, Westbrook, CT (US); Abu Sayed, East Lyme, CT (US); Mangkey A. Bounpheng, Austin, TX (US); Thomas G. Burrage, Guilford, CT (US); Brooke A. Dancho, Athens, GA (US); Sabena Uddowla Blakeney, Lanham, MD (US)

(73) Assignees: THE TEXAS A&M UNIVERSITY SYSTEM, College Station, TX (US); THE UNITED STATES OF AMERICA, AS REPRESENTED BY THE SECRETARY OF AGRICULTURE, Washington, DC (US); THE UNITED STATES OF AMERICA, AS REPRESENTED BY THE SECRETARY OF HOMELAND SECURITY, Washington, DC (US)

( * ) Notice: Subject to any disclaimer, the term of this patent is extended or adjusted under 35 U.S.C. 154(b) by 0 days.

(21) Appl. No.: 15/010,278

(22) Filed: Jan. 29, 2016

(65) Prior Publication Data
US 2017/0218053 A1    Aug. 3, 2017

(51) Int. Cl.
*C07K 16/10* (2006.01)
*G01N 33/53* (2006.01)
*G01N 33/569* (2006.01)

(52) U.S. Cl.
CPC ... *C07K 16/1009* (2013.01); *G01N 33/56983* (2013.01); *C07K 2317/34* (2013.01); *C07K 2319/21* (2013.01); *C12N 2770/32122* (2013.01); *C12N 2770/32134* (2013.01); *G01N 2333/09* (2013.01)

(58) Field of Classification Search
None
See application file for complete search history.

(56) References Cited

U.S. PATENT DOCUMENTS

2011/0014639 A1*  1/2011  Chen ................. C07K 16/1009
                                                    435/7.94

OTHER PUBLICATIONS

Ahmad et al., Hindawi Publishing Corporation, Clinical and Developmental Immunology, 2012, vol. 2012, Article ID 980250, 15 pages.*
Höhlich, B.-J. et al. "Identification of Foot-and-Mouth Disease Virus-Specific Linear B-Cell Epitopes to Differentiate between Infected and Vaccinated Cattle" *Journal of Virology*, Aug. 2003, pp. 8633-8639, vol. 77, No. 16.
Oem, J. K. et al. "Development of an epitope-blocking-enzyme-linked immunosorbent assay to differentiate between animals infected with and vaccinated against foot-and-mouth disease virus" *Journal of Virological Methods*, 2007, pp. 174-181, vol. 142.
Thermo Scientific Crosslinking Technical Handbook, "easy molecular bonding—crosslinking technology—Reactivity chemistries, applications and structure references" *Thermo Fisher Scientific Inc.*, 2012, pp. 1-54.
Yang, M. et al. "Development of a Competitive Enzyme-Linked Immunosorbent Assay for Detection of Antibodies against the 3B Protein of Foot-and-Mouth Disease Virus" *Clinical and Vaccine Immunology*, Apr. 2015, pp. 389-397, vol. 22, No. 4.

* cited by examiner

*Primary Examiner* — Stacy B Chen
(74) *Attorney, Agent, or Firm* — Saliwanchik, Lloyd & Eisenschenk

(57) ABSTRACT

This disclosure pertains to isolated antibodies or antigen binding fragments thereof that specifically bind to the 3ABC non-structural protein of Foot-and-Mouth Disease virus (FMDV), wherein the antibodies or antigen binding fragments thereof recognize the amino acid sequence of SEQ ID NO: 2, SEQ ID NO: 3, SEQ ID NO: 4, SEQ ID NO: 5, SEQ ID NO: 6 or SEQ ID NO: 12. Accordingly, this disclosure also pertains to polypeptides having an amino acid sequence selected from SEQ ID NO: 2, SEQ ID NO: 3, SEQ ID NO: 4, SEQ ID NO: 5 or SEQ ID NO: 12. Monoclonal antibody Mab 40C8 is also provided. The current disclosure also pertains to methods of detecting FMDV infection in an animal (including assays differentiating infected animals from vaccinated animals (DIVA)) and kits for performing the detection methods. Competitive ELISA kits comprising the antibody or antigen binding fragment thereof and immunoassay plates coated with the polypeptide comprising the amino acid sequence selected from SEQ ID NO: 2, SEQ ID NO: 3, SEQ ID NO: 4, SEQ ID NO: 5, SEQ ID NO: 6 and/or SEQ ID NO: 12 are also provided.

19 Claims, 15 Drawing Sheets
(8 of 15 Drawing Sheet(s) Filed in Color)

| | O | % | A | % | C | % | ASIA1 | % | SAT1 | % | SAT2 | % | SAT3 | % | Total |
|---|---|---|---|---|---|---|---|---|---|---|---|---|---|---|---|
| *GPYAGPLERQKPLK | 99 | 56 | 53 | 78 | 5 | 21 | 40 | 93 | | 0 | | 0 | | 0 | 197 |
| GPYTGPLERQKPLK | 66 | 37 | 2 | 3 | | 0 | 1 | 2 | | 0 | | 0 | | 0 | 69 |
| GPYAGPLERQRPLK | 5 | 3 | 7 | 10 | 18 | 75 | | 0 | | 0 | | 0 | | 0 | 30 |
| GPYAGPLERQQPLK | | 0 | | 0 | | 0 | | 0 | 7 | 78 | 3 | 50 | 4 | 100 | 14 |
| GPYTGPLERQRPLK | | 0 | 3 | 4 | 1 | 4 | | 0 | 1 | 11 | | 0 | | 0 | 5 |
| GPYAGPMERQKPLK | | 0 | | 0 | | 0 | | 0 | 1 | 11 | 3 | 50 | | 0 | 4 |
| GPYVGPLERQKPLK | 3 | 2 | | 0 | | 0 | | 0 | | 0 | | 0 | | 0 | 3 |
| GPYSGPLERQKPLK | | 0 | 1 | 1 | | 0 | | 0 | | 0 | | 0 | | 0 | 1 |
| GPYGGPLERQKPLK | | 0 | 1 | 1 | | 0 | | 0 | | 0 | | 0 | | 0 | 1 |
| GPYAGPVERQKPLR | 1 | 1 | | 0 | | 0 | | 0 | | 0 | | 0 | | 0 | 1 |
| GPYAGPLERQKPLT | 1 | 1 | | 0 | | 0 | | 0 | | 0 | | 0 | | 0 | 1 |
| GPYAGPLERQKPLR | 1 | 1 | | 0 | | 0 | | 0 | | 0 | | 0 | | 0 | 1 |
| GPYAGPLERQKPLQ | 1 | 1 | | 0 | | 0 | | 0 | | 0 | | 0 | | 0 | 1 |
| GPYAGPLERQKPLE | | 0 | | 0 | | 0 | 1 | 2 | | 0 | | 0 | | 0 | 1 |
| GPYAGPLERQIPLK | | 0 | 1 | 1 | | 0 | | 0 | | 0 | | 0 | | 0 | 1 |
| GPYAGAFERQKTLK | | 0 | | 0 | | 0 | 1 | 2 | | 0 | | 0 | | 0 | 1 |
| | 177 | 100 | 68 | 100 | 24 | 100 | 43 | 100 | 9 | 100 | 6 | 100 | 4 | 100 | 331 |

* peptide used for Mab production

Figure 2

MAB 40C8 TVMDL

| Peptide | OD 1 | OD 2 | Avg | pepCtrlOD | ODMab-ODCrtol | Pep/pepRef | peptide# |
|---|---|---|---|---|---|---|---|
| GPYAGPLERQKPLK | 1.36 | 1.33 | 1.34 | 0.15 | 1.19 | 1.00 | 1 |
| GPYTGPLERQKPLK | 2.18 | 2.44 | 2.31 | 0.15 | 2.16 | 1.81 | 2 |
| GPYAGPLERQRPLK | 1.24 | 1.27 | 1.26 | 0.15 | 1.11 | 0.93 | 3 |
| GPYAGPLERQQPLK | 1.31 | 1.39 | 1.35 | 0.15 | 1.20 | 1.01 | 4 |
| GPYTGPLERQRPLK | 2.34 | 2.43 | 2.39 | 0.15 | 2.24 | 1.88 | 5 |
| GPYAGPMERQKPLK | 2.52 | 2.55 | 2.53 | 0.15 | 2.38 | 2.00 | 6 |
| GPYVGPLERQKPLK | 2.23 | 2.32 | 2.28 | 0.15 | 2.13 | 1.79 | 7 |
| GPYSGPLERQKPLK | 2.17 | 2.09 | 2.13 | 0.15 | 1.98 | 1.67 | 8 |
| GPYGGPLERQKPLK | 2.70 | 2.83 | 2.77 | 0.15 | 2.62 | 2.20 | 9 |
| GPYAGPVERQKPLR | 2.03 | 2.14 | 2.09 | 0.15 | 1.94 | 1.63 | 10 |
| GPYAGPLERQKPLT | 1.23 | 1.23 | 1.23 | 0.15 | 1.08 | 0.91 | 11 |
| GPYAGPLERQKPLR | 1.36 | 1.29 | 1.33 | 0.15 | 1.18 | 0.99 | 12 |
| GPYAGPLERQKPLQ | 1.21 | 1.17 | 1.19 | 0.15 | 1.04 | 0.87 | 13 |
| GPYAGPLERQKPLE | 1.17 | 1.17 | 1.17 | 0.15 | 1.02 | 0.86 | 14 |
| GPYAGPLERQIPLK | 1.37 | 1.37 | 1.37 | 0.15 | 1.22 | 1.03 | 15 |
| GPYAGAFERQKTLK | 0.90 | 0.91 | 0.91 | 0.15 | 0.76 | 0.63 | 16 |

Figure 4

MAB F38B Winnipeg

| Peptide | OD 1 | OD 2 | Avg | control OD | ODMab-ODCrtol | Pep/pepRef | peptide# |
|---|---|---|---|---|---|---|---|
| GPYAGPLERQKPLK | 1.69 | 1.73 | 1.71 | 0.13 | 1.58 | 1.00 | 1 |
| GPYTGPLERQKPLK | 1.33 | 1.25 | 1.29 | 0.13 | 1.16 | 0.74 | 2 |
| GPYAGPLERQRPLK | 1.96 | 1.77 | 1.86 | 0.13 | 1.73 | 1.10 | 3 |
| GPYAGPLERQQPLK | 1.83 | 1.82 | 1.82 | 0.13 | 1.69 | 1.07 | 4 |
| GPYTGPLERQRPLK | 1.21 | 1.17 | 1.19 | 0.13 | 1.06 | 0.67 | 5 |
| GPYAGPMERQKPLK | 1.71 | 1.68 | 1.69 | 0.13 | 1.56 | 0.99 | 6 |
| GPYVGPLERQKPLK | 1.26 | 1.40 | 1.33 | 0.13 | 1.20 | 0.76 | 7 |
| GPYSGPLERQKPLK | 1.75 | 1.91 | 1.83 | 0.13 | 1.70 | 1.08 | 8 |
| GPYGGPLERQKPLK | 1.65 | 1.64 | 1.64 | 0.13 | 1.51 | 0.96 | 9 |
| GPYAGPVERQKPLR | 0.75 | 0.82 | 0.78 | 0.13 | 0.65 | 0.41 | 10 |
| GPYAGPLERQKPLT | 1.38 | 1.40 | 1.39 | 0.13 | 1.26 | 0.80 | 11 |
| GPYAGPLERQKPLR | 1.79 | 1.66 | 1.72 | 0.13 | 1.59 | 1.01 | 12 |
| GPYAGPLERQKPLQ | 1.48 | 1.46 | 1.47 | 0.13 | 1.34 | 0.85 | 13 |
| GPYAGPLERQKPLE | 1.29 | 1.24 | 1.26 | 0.13 | 1.13 | 0.72 | 14 |
| GPYAGPLERQIPLK | 1.63 | 1.71 | 1.67 | 0.13 | 1.54 | 0.97 | 15 |
| GPYAGAFERQKTLK | 0.10 | 0.12 | 0.11 | 0.13 | -0.02 | -0.01 | 16 |

| | | | | | | |
|---|---|---|---|---|---|---|
| FMDV A₁₂ | FMDV O1 Campos | FMDV O1UK | FMDV SAT2 | FMDV C3 Resende | Mock | FMDV A₂₄ |

52kDa — 3D

28kDa — 3ABBB
                3ABB
                3B (40C8)
17kDa — 3AB

Infected BHK cell lysates

Figure 7B

A22 IRAQ | A IRAN | A Egypt | Malaysia | A24 SDG | Asia Shamir | C3R | O1C | O1M | O Ecuador | Hong Kong | SAT-2 | SAT-3 | Mock 28kDa — mAb 40C8
1:500

MONOCLONAL ANTIBODY AGAINST NOVEL EPITOPES OF FOOT-AND-MOUTH DISEASE VIRUS PROTEIN 3ABC AND USES THEREOF

This invention was made with Government support under HSHQDC-11-X-00189 and HSHQDC-09-X-00369 awarded by the United States Department of Homeland Security Science and Technology (DHS S&T) to the U.S. Department of Agriculture, and under 2007-ST-061-000002-02 and HSHQDC-11-J-00452, awarded by DHS S&T to Texas A&M AgriLife Research. The Government has certain rights in the invention.

The Sequence Listing for this application is labeled "Seq-List-replace.txt" which was created on Dec. 15, 2017 and is 27 KB. The entire contents of the sequence listing is incorporated herein by reference in its entirety.

BACKGROUND

Foot-and-mouth disease (FMD) is a highly contagious viral disease (Foot-and-Mouth Disease Virus (FMDV)) that may affect domestic (e.g., cattle, swine, sheep, and goats) and wild (e.g., deer, bison, pronghorn antelope, and feral swine) cloven-hoofed animals. The disease is characterized by fever, vesicular (blister-like) lesions, and subsequent erosions (ulcers) of the surfaces of the mouth, tongue, nostrils, muzzle, feet, and teats. FMD does not typically kill adult livestock, but it does have very detrimental effects on productivity (meat and milk) and high mortality rates may occur in young animals.

FMD is caused by the FMD virus (FMDV) of the Aphthovirus genus in the Picornaviridae family. There are seven different serotypes of FMDV: O, A, C, Southern African Territories [SAT] 1, SAT 2, SAT 3 and Asia 1. Multiple serotypes co-circulate around the world; six out of the seven serotypes have been recorded in Africa (O, A, C, SAT 1, SAT 2, SAT 3), while four serotypes (O, A, C, Asia 1) have been documented in the Middle East and Asia. O serotype is most common, followed by Asia 1. All serotypes are immunologically distinct but produce clinically indistinguishable disease. There is no cross protection between serotypes.

Primary infection of ruminants is mainly by the respiratory route, whereas infection of pigs is usually through the oral route. Infection results in production of protective serotype specific antibodies against FMDV structural proteins 5 to 14 days post-infection. Transmission of FMDV mainly occurs through direct contact between infected and susceptible animals. Indirect transmission is also possible through fomites contaminated with secretions and excretions from infected animals. FMDV can be found in secretions and excretions such as expired air, saliva, nasal secretions, milk, urine, feces, and semen from acutely infected animals. Shedding can occur up to 4 days prior to the onset of clinical signs. Aerosol transmission also occurs, particularly through pigs that excrete large amounts of virus through their respiratory tract, resulting in infectious aerosols that can be inhaled by other animals in proximity.

FMD is present in about two-thirds of the world and endemic in parts of Africa, Asia, the Middle East, and South America. The global economic impact is colossal due to direct losses associated with reduced production efficiency and changes in herd structure, and indirect losses associated with cost of control strategies, and loss of international trade status. The estimated annual economic impact of FMD in production losses and vaccination cost in endemic regions is estimated between $6.5 and $21 billion USD, and $1.5 billion USD in FMD free countries if outbreaks occurred, based on reported loss of $20 billion USD during the last 15 years in countries that were previously considered FMD-free. The United States has been FMD-free since 1929. However, there are many susceptible animals in the United States, including approximately 94.5 million cattle, 67 million swine, and 8.5 million sheep and goats. An outbreak of FMD in the U.S. would have a devastating economic impact, due to the loss of international trade, production lost, and costs associated with depopulation, disposal, and disinfection. Diagnostic testing capabilities to differentiate infected and vaccinated animals (DIVA) are necessary to support emergency vaccination strategies. To this end, there is a need for reagents that enables FMD serological testing in the US mainland. The current disclosure provides antibodies, peptides, and kits for detection of FMDV infections and differentiation of FMDV infected animals from FMDV vaccinated animals.

BRIEF SUMMARY

The current disclosure provides isolated antibodies or antigen binding fragments thereof that specifically bind to the 3ABC non-structural protein of Foot-and-Mouth Disease Virus (FMDV), wherein the antibodies or antigen binding fragments thereof recognize the amino acid sequence of SEQ ID NO: 3, SEQ ID NO: 4, SEQ ID NO: 5 or SEQ ID NO: 12 as an epitope. Accordingly, the current disclosure provides polypeptides providing a novel epitope from FMDV protein 3ABC. The epitope has the amino acid sequence set forth in SEQ ID NO: 3, SEQ ID NO: 4, SEQ ID NO: 5 or SEQ ID NO: 12. The antibodies or antigen binding fragments thereof can be monoclonal antibodies (Mab), chimeric antibodies, single chain antibodies, single chain fragment variable (scFv) antibodies, or fragment antigen-binding (Fab fragment). In an embodiment, the antibody is Mab 40C8 as produced by hybridoma which is deposited with the American Type Culture Collection with Designation: PTA-122531.

The current disclosure also provides methods of detecting Foot-and-Mouth Disease virus (FMDV) infection in an animal, the method comprising performing an assay using the polypeptides (epitope sequences) disclosed herein or antibodies or antigen binding fragments thereof that bind the disclosed polypeptides on a biological sample obtained from the animal. The assay can be an enzyme-linked immunosorbent assay (ELISA), for example, sandwich ELISA or competitive ELISA. An infected animal may be infected naturally (e.g., animals at commercial farms, etc.) or experimentally (e.g., in laboratories or experimental facility).

The current disclosure also provides kits, for example ELISA kits, comprising the antibody or antigen binding fragment thereof. The antibodies or antigen binding fragments thereof can be labeled with an enzyme in the ELISA kits. Alternately, the antibodies or antigen binding fragments thereof can be coated onto immunoassay plates. The kits can further comprise an immunoassay plate coated with the polypeptide comprising the amino acid sequence selected from SEQ ID NO: 2, SEQ ID NO: 3, SEQ ID NO: 4, SEQ ID NO: 5 or SEQ ID NO: 12.

Further, the current disclosure provides antibodies or antigen binding fragments thereof obtained from an animal that has been immunized with a polypeptide comprising an amino acid sequence selected from SEQ ID NO: 3, SEQ ID NO: 4, SEQ ID NO: 5 or SEQ ID NO: 12, and wherein the antibodies or antigen binding fragments thereof recognize the amino acid sequence of SEQ ID NO: 3, SEQ ID NO: 4, SEQ ID NO: 5 or SEQ ID NO: 12 as an epitope.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 2 shows a sequence analysis of 331 strains from GenBank which revealed up to 20% variability in the 3ABC epitope. The sequences are presented as SEQ ID NOs: 13-28.

FIG. 4 shows that Mab 40C8 exhibited positive reactivity to diverse 3ABC peptide variants. The sequences are presented as SEQ ID NOs: 13-28.

FIGS. 7A and 7B show western blot analysis using Mab 40C8 antibody to detect various serotypes of FMDV. As a control the infected cell-lysates were also examined using a monoclonal antibody (F19-2) specific to the FMDV 3D polymerase.

FIG. 11 shows detection of antibodies by the 3ABC ELISA following Infection of cattle with one of four serotypes of FMDV (n=4 animals/serotype; data averaged).

FIG. 12 shows detection of antibodies to the FMDV 3ABC non-structural proteins in cattle vaccinated with Ad-A24.

BRIEF DESCRIPTION OF THE SEQUENCES

Figure 1:
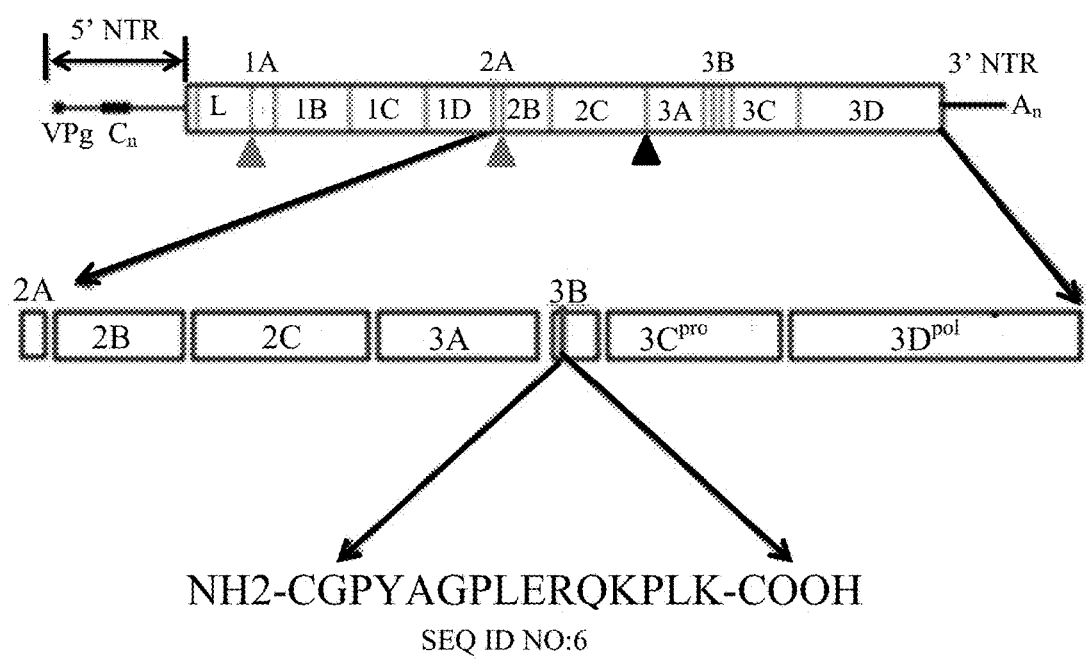
FIG. 1 shows sequence and location of the epitope (SEQ ID NO: 3) bound by the 40C8 antibody within the FMDV protein. The sequence in FIG. 1 includes a N-terminal cysteine residue used to conjugate the epitope to a carrier protein and is presented as SEQ ID NO: 6).

SEQ ID NO: 1: Sequence of 3ABC protein from FMDV serotype O.

SEQ ID NO: 2: Amino acid sequence for the 3ABC recombinant protein designated PET31b3b12X.

SEQ ID NO: 3: Sequence of the epitope for Mab 40C8 binding. (Sequence: GPYAGPLERQKPLK).

SEQ ID NO: 4: Sequence of the minimal epitope for Mab 40C8 binding. (Sequence: GPLERQ).

SEQ ID NOs: 5 and 12: Alternate sequence of the minimal epitopes for MAB 40C8 binding, where X is any amino acid. (Sequence: G $X_1X_2$ERQ; GPYAG$X_1X_2$ERQKPLK).

SEQ ID NO: 6: FMDV peptide for generation of Mab 40C8 antibody with amino terminal cysteine added. (Sequence: CGPYAGPLERQKPLK).

SEQ ID NO: 7: Forward PCR primer for overlap extension PCR of 3ABC cDNA. (Sequence: CAATTCCTTC-CCAAAAATCT).

SEQ ID NO: 8: Reverse PCR primer for overlap extension PCR of 3ABC cDNA. (Sequence: GTGGTGTGGT-TCGGGGTCCAA).

SEQ ID NO: 9: Nucleotide sequence of plasmid pET30c O1C 3ABC* (3C mutation at nucleotide 6381: T to C, Cysteine to Arginine).

SEQ ID NO: 10: Nucleotide sequence encoding O1C 3ABC* (3C mutant at nucleotide 1239; T to C, Cysteine to Arginine).

SEQ ID NO: 11: Amino acid sequence corresponding to the serotype O FMDV 3ABC* mutant protein containing a His6 tag for expression and purification from *Escherichia coli* (3C mutant at amino acid 163: Cysteine to Arginine).

SEQ ID NOs: 13-28: Peptide sequences disclosed in FIGS. 2 and 4.

DETAILED DISCLOSURE

Overview

We have developed a monoclonal antibody (40C8) specific for the FMDV nonstructural protein (NSP) 3ABC polypeptide and have demonstrated broad reactivity of this antibody against bovine sera from all seven FMDV serotypes. This monoclonal antibody may be used for FMDV serological diagnostics (including differentiation between infected and vaccinated animals (DIVA) capability) and attenuated FMD vaccine production quality control testing.

Foot-and-mouth disease (FMD) serological testing in the U.S. is currently performed only at the USDA Animal and Plant Health Inspection Service (APHIS) Foreign Animal Disease Diagnostic Laboratory (FADDL) at Plum Island Animal Disease Center (PIADC) under an experimental research and evaluation permit using an ELISA kit. The current disclosure provides antibodies, peptides, and kits for detection of FMDV infections and differentiation of FMDV infected animals from FMDV vaccinated animals.

DISCLOSURE

ATCC information: The hybridoma cell line which can be used to produce Mab 40C8 was deposited with American Type Culture Collection (ATCC), P.O. Box 1549, Manassas, Va. 20108, on Sep. 29, 2015 (ATCC Designation PTA-122531). The subject hybridoma cell line has been deposited under conditions that assure that access to the cell line will be available during the pendency of this patent application to one determined by the Commissioner of Patents and Trademarks to be entitled thereto under 37 C.F.R. 1.14 and 35 U.S.C. § 122. This deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.

The current disclosure provides a novel epitope of the 3ABC protein from FMDV, for example, an epitope having the amino acid sequence of SEQ ID NO: 3, SEQ ID NO: 4, SEQ ID NO: 5 or SEQ ID NO: 12 (or any polypeptide disclosed in FIG. 4), and antibodies and antigen binding fragments thereof that specifically recognize one of these epitopes. This disclosure also describes methods, techniques, approaches, kits for use in conjunction with the present disclosure.

The current disclosure also provides methods of using the antibodies or antigen binding fragments thereof and the novel epitopes for detection for FMDV infection in animals and for distinguishing FMDV infected animals from animals vaccinated against FMDV infection. The methods of the current disclosure provide improved sensitivity and specificity over the existing methods of detection of FMDV in animals and reduces the time necessary to identify animals having a positive serotype for FMDV.

Accordingly, the current disclosure provides antibodies and antigen binding fragments thereof that specifically binds to the 3ABC non-structural protein of FMDV, wherein the antibodies or antigen binding fragments thereof recognize the amino acid sequence of SEQ ID NO: 3, SEQ ID NO: 4, SEQ ID NO: 5 or SEQ ID NO: 12 (or any polypeptide disclosed in FIG. 4) as an epitope. In some embodiments, antibodies bind to the same epitope as the monoclonal antibody produced by the hybridoma 40C8. Such antibodies can be identified using any one of a variety of immunological screening assays in which antibody competition can be assessed. In an embodiment, the antibody is a monoclonal antibody. Additionally, the antibodies can be polyclonal antibodies. In further embodiments, the antibody or antigen binding fragments thereof can be chimeric antibodies, single chain antibodies, scFv antibodies, or Fab fragments.

Thus, one embodiment provides a monoclonal antibody, Mab 40C8, as produced by hybridoma cell line deposited with the American Type Culture Collection with Designation: PTA-122531.

A further embodiment provides antibodies or antigen binding fragments thereof obtained from an animal that has been immunized with a polypeptide comprising an amino acid sequence selected from SEQ ID NO: 4, SEQ ID NO: 5 or SEQ ID NO: 12 (or any polypeptide disclosed in FIG. 4), and wherein the antibodies or antigen binding fragments thereof recognize the amino acid sequence of SEQ ID NO: 3, SEQ ID NO: 4, SEQ ID NO: 5 or SEQ ID NO: 12 (or the immunizing polypeptide from FIG. 4) as an epitope. These antibodies can also be monoclonal antibodies or polyclonal antibodies.

The antibodies and antigen binding fragments thereof can be used in an assay to detect the presence or absence in a sample of 3ABC protein from FMDV, for example by a Western blot analysis or a sandwich ELISA; to detect the presence in a sample of antibodies against 3ABC protein from FMDV, for example, by a competitive ELISA; or to detect the presence of FMDV infection in an animal, for example, by a western blot analysis or an ELISA. The antibodies and antigen binding fragments thereof can also be used to distinguish the animals infected with FMDV from the animals vaccinated against FMDV. Accordingly, the current disclosure provides methods of detecting the presence of 3ABC protein, or antibodies against 3ABC proteins and thus detect the presence of FMDV infection in an animal.

The detection of the presence of 3ABC protein, or the antibodies against 3ABC proteins can be facilitated by conjugating/coupling the antibodies and antigen binding fragments thereof to appropriate labels. Non-limiting examples of labels that can be conjugated to the antibodies or antigen binding fragments thereof as disclosed herein include an enzyme, a radioisotope, a fluorescent label, or a bioluminescent label. Additional embodiments of labels that can be conjugated/coupled to the antibodies and antigen binding fragments thereof of the current disclosure and various methods of detecting the labels are recognized.

Various assays for detection of 3ABC proteins can be used to detect FMDV infection in an animal using the antibodies or antigen binding fragments thereof of the current disclosure. Non-limiting examples of protein detection assays include Western blot analysis, ELISA, immunohistochemistry, or immunoprecipitation. Additional examples of assays utilizing antibodies or antigen binding fragments thereof to detect the presence of specific proteins or specific antibodies in samples are recognized.

Assays disclosed herein can be used to detect the 3ABC protein, or antibodies against 3ABC proteins can be performed on a biological sample obtained from an animal. In certain embodiments, the biological sample obtained from the animal contains the 3ABC proteins derived from FMDV or the antibodies produced in the body of the animal against 3ABC proteins. In embodiments the biological sample is a body-fluid sample or a tissue sample. It should be appreciated that the assays may be used as part of an approach to determine the absence of the 3 ABC protein in some instances.

This disclosure also provides methods of screening a population of animals for FMDV infection, an exemplary method includes:

a) obtaining a biological sample from each animal from the population of animals, b) conducting an assay comprising contacting said biological sample with an 3ABC polypeptide or a polypeptide comprising SEQ ID NO: 2, SEQ ID NO: 3, SEQ ID NO: 4, SEQ ID NO: 5, any polypeptide disclosed in FIG. 4 or SEQ ID NO: 12, said polypeptide being optionally bound to a substrate, using an antibody or an antigen binding fragment thereof to distinguish FMDV infected animals from animals vaccinated against FMDV infection, wherein the antibody or the antigen binding fragment thereof recognizes the amino acid sequence of SEQ ID NO: 3, SEQ ID NO: 4, SEQ ID NO: 5, any polypeptide disclosed in FIG. 4 or SEQ ID NO: 12 as an epitope, and c) identifying individual animals from the population of animals as FMDV infected animals or FMDV vaccinated animals. In certain embodiments, the assay is performed using the kit according to the current disclosure. In a further embodiment, the animal screened for FMDV infection is at least one of cattle, buffalo, water buffalo, sheep, goat, antelope, deer, bison, elephant, llama, or alpaca. The sample obtained from the animal can be any biological sample described above. Additional embodiments provide for the optional quarantine or slaughter of infected animals.

Non-limiting examples of biological samples (e.g., body fluid samples) include aqueous humor, vitreous humor, blood serum, blood plasma, cerebrospinal fluid, endolymph, perilymph, exudates, lymph, mucus, pericardial fluid, pleural fluid, synovial fluid, milk, or oral fluids. Non-limiting examples of tissue samples include brain, eyes, pineal gland, pituitary gland, thyroid gland, parathyroid glands, thorax, heart, lungs, esophagus, thymus gland, pleura, adrenal glands, appendix, gall bladder, urinary bladder, large intestine, small intestine, kidneys, liver, pancrease, spleen, stoma, prostate gland, testes, ovaries, or uterus. The tissue samples can be appropriately processed to produce a sample suitable for performing the assay for detection of the 3ABC protein, or antibodies against 3ABC proteins. It is to be apparent that the foregoing method can also be used to identify animals that have been innoculated for protection against FMD as is understandable to a person of ordinary skill.

The current disclosure further provides kits containing the antibodies or antigen binding fragments thereof. A kit, for example, is used to detect the presence in a sample of 3ABC protein, to detect the presence in a sample of antibodies against 3ABC protein from FMDV, or to detect the presence of FMDV infection in an animal. Using the antibodies or antigen binding fragments described herein, a person of ordinary skill in the art can design various assays for different purposes in accordance with this disclosure, for example, to detect the presence of 3ABC protein, to detect the presence of antibodies against 3ABC protein, or to detect the presence of FMDV infection in an animal. Antibodies that bind to an epitope defined by any one of SEQ ID NO: 3, 4, 5 or 12 are also expected to bind to proteins containing this epitope (e.g., the 3B, 3AB, 3ABC or the recombinant protein of SEQ ID NO: 2).

The kits in accordance with this disclosure can comprise reagents for conducting various assays. The reagents provided in a kit depend on the purpose and design of the assay to be performed. For example, a kit designed for a western blot analysis contains a labeled secondary antibody and additional reagents for visualizing the label. Various embodiments of western blot analyses are contemplated.

Kits for performing ELISA are also disclosed. The kits can be designed to perform different types of ELISA, for example, a sandwich ELISA or a competitive ELISA. A person of ordinary skill in the art knows various reagents and tools required for conducting each of the different types of ELISAs and accordingly, the current disclosure provides kits containing appropriate reagents and tools for performing these ELISAs.

For example, a kit for conducting a sandwich ELISA can contain an immunoassay plate coated with the antibodies or antigen binding fragments thereof disclosed herein. The sandwich ELISA kit can further contain 3ABC antibodies directed to different epitopes than the epitopes of the current disclosure. These different antibodies can be conjugated to an enzyme. The sandwich ELISA kit can further contain reagents for carrying out and visualizing the enzymatic reaction catalyzed by the conjugated enzyme.

A person of ordinary skill in the art with this disclosure can design various embodiments of a sandwich ELISA kit using the antibodies or antigen binding fragments thereof disclosed herein. For example, instead of coating the immunoassay plate with the antibodies or antigen binding fragments thereof, a kit contains immunoassay plate coated with antibodies against 3ABC epitopes different from the epitopes disclosed herein and enzymatically labeled antibodies or antigen binding fragments thereof of the current disclosure. Alternately, enzyme linked secondary antibodies can also be provided. Additional designs of ELISAs can be envisioned based on the present disclosure.

A further embodiment of this disclosure provides a kit for performing cELISA for detection of antibodies against 3ABC protein in a sample, for example a biological sample obtained from an animal. The USDA and Department of Homeland Security (DHS) Science and Technology research teams at Plum Island Animal Disease Center (PIADC) have developed the first bioengineered vaccine against FMDV that can be produced in the U.S. The cELISA kit of the current disclosure provides a companion diagnostic tool for a U.S.-based FMD vaccination program that utilizes FMD vaccines lacking a full-length 3ABC protein. Therefore, the kit can be used to detect FMDV infection in animals and can also differentiate infected animals from vaccinated animals, animals vaccinated for immunity to FMDV. For example, animals vaccinated with FMD vaccines lacking a full-length 3ABC protein or FMD vaccines that do not code for the FMDV 3ABC protein lack antibodies that bind to the 3ABC polypeptide or the epitope bound by the antibodies disclosed herein. Thus, such animals should not have antibodies that bind to a polypeptide disclosed herein and such animals should not have antibodies that compete with the disclosed antibodies (e.g., such animals should have no antibodies that compete with the 40C8 monoclonal antibody (or antibodies that bind to the same epitope as the 40C8 antibody) for binding to a peptide as disclosed herein or the 3ABC polypeptide).

The cELISA kit described herein can provide a fast FMD serological assay which provides results in hours rather than days, as well as superior specificity and sensitivity compared to a commercial product. The cELISA kit of the current disclosure also provides a differentiation between infected and vaccinated animals (DIVA) test for the adenovirus serotype 5 FMD vaccine (and future vaccines that lack FMDV 3ABC immunogenic proteins. Certain aspects of this disclosure provide polypeptides useful for making antibodies or in competitive immunoassays. With respect to the amino acid sequences set forth in SEQ ID NO: 5 and SEQ ID NO: 12, $X_1$ and $X_2$ can be any amino acid (as set forth in Table 1), provided that if $X_1$ is proline, then $X_2$ cannot be leucine and if $X_2$ is leucine, then $X_1$ cannot be proline (e.g., SEQ ID NO: 12 specifically excludes the amino acid sequence of SEQ ID NO: 3 as a possible sequence). Another embodiment provides, with respect to the amino acid sequences set forth in SEQ ID NO: 5 and SEQ ID NO: 12, that $X_1$ and $X_2$ can be any amino acid (as set forth in Table 1), provided that if $X_1$ is proline, then $X_2$ cannot be methionine. Other non-limiting examples of polypeptides are provided in FIG. 4). In some other embodiments, polypeptides in which a cysteine (C) is found at the amino terminus of the polypeptide are also provided (e.g., SEQ ID NO: 6). Polypeptides containing a cysteine residue at the amino terminus of the polypeptide are suitable for covalent attachment to a carrier protein via another cysteine residue or various linkers.

TABLE 1

20 amino acids and single letter codes (SLC)

| Amino Acid | SLC |
|---|---|
| Isoleucine | I |
| Leucine | L |
| Valine | V |
| Phenylalanine | F |
| Methionine | M |
| Cysteine | C |
| Alanine | A |
| Glycine | G |
| Proline | P |
| Threonine | T |
| Serine | S |
| Tyrosine | Y |
| Tryptophan | W |
| Glutamine | Q |
| Asparagine | N |
| Histidine | H |

TABLE 1-continued 20 amino acids and single letter codes (SLC)

| Amino Acid | SLC |
|---|---|
| Glutamic acid | E |
| Aspartic acid | D |
| Lysine | K |
| Arginine | R |

In another aspect, immunoassays using the disclosed polypeptides or antibodies are provided. In embodiments in accordance with this aspect, antibodies that bind to an epitope comprising SEQ ID NO: 3, 4, 5 or 12 (or the polypeptides disclosed in FIG. 4) or a polypeptide selected from SEQ ID NO: 2, 3, 4, 5 or 12 (or polypeptides disclosed in FIG. 4) are bound to a substrate. The term "bound" refers to both covalent and non-covalent attachment of an antibody or polypeptide to a substrate. Thus, antibodies or polypeptides can be covalently bound to the substrate via a linker physically attached to a substrate or non-covalently bound to a substrate (e.g., adsorbed to a substrate surface, for example, a polystyrene surface).

In various embodiments, the substrate is one or more tubes, cylinders, beads, discs, silicon chips, microplates, polyvinylidene difluoride (PVDF) membrane, nitrocellulose membrane, nylon membrane, porous membranes, non-porous membranes, plastic, polymer, silicon, polymeric pins, a plurality of microtiter wells, or combinations thereof. The composition of the substrate can also be varied. Substrates (alternatively referred to as a support) can comprise glass, cellulose-based materials, thermoplastic polymers, such as polyethylene, polypropylene, or polyester, sintered structures composed of particulate materials (e.g., glass or various thermoplastic polymers), or cast membrane film composed of nitrocellulose, nylon, polysulfone, or the like. Thus, the substrate may be any surface or support upon which an antibody or a polypeptide selected from those disclosed in FIG. 4 or SEQ ID NOs: 2, 3, 4, 5, 6 and/or 12 can be immobilized, including one or more of a solid support (e.g., glass such as a glass slide or a coated plate, silica, plastic or derivatized plastic, paramagnetic or non-magnetic metal), a semi-solid support (e.g., a polymeric material, a gel, agarose, or other matrix), and/or a porous support (e.g., a filter, a nylon or nitrocellulose membrane or other membrane). In some embodiments, synthetic polymers is used as a substrate, including, e.g., polystyrene, polypropylene, polyglycidylmethacrylate, aminated or carboxylated polystyrenes, polyacrylamides, polyamides, polyvinylchlorides, and the like. In preferred embodiments, the substrate comprises a microtiter immunoassay plate or other surface suitable for use in an ELISA.

In embodiments, polypeptides have additional material covalently linked to either or both ends of the polypeptide (e.g., additional amino acids to the amino acid sequence of interest), provided that, in the case of SEQ ID NOs: 3, 4, 5, 6 or 12 (or the polypeptides disclosed in FIG. 4), the additional amino acids do not provide the sequence of the FMDV 3ABC or any other naturally occurring polypeptide containing SEQ ID NO: 3, 4, 5 or 12 (or sequence as disclosed in FIG. 4). Covalent linkage of additional amino acids to either or both ends of the polypeptide disclosed herein results in a combined amino acid sequence that is not naturally occurring, e.g. an unnatural amino acid sequence that is not found in nature. Polypeptides include a polypeptide having an amino acid sequence selected from the group consisting of SEQ ID NO: 4, 5, 6 or 12 (or any polypeptide disclosed in FIG. 4) coupled to a carrier protein (e.g., a carrier such as an albumin (e.g., bovine serum albumin), keyhole limpet hemocyanin, ovalbumin). Such coupling can be a covalent linkage. These peptides are rendered immunogenic by coupling them to an immunogenic carrier by the following procedure.

An immunizing agent is constructed by covalently conjugating a polypeptide selected from the polypeptides disclosed in FIG. 4, SEQ ID NOs: 4, 5, 6 and/or 12 to an immunogenic carrier protein, preferably by means of a crosslinker, such as a glutaraldehyde moiety or other known linkers. Immunogenic carriers include compounds to which any one of the peptides disclosed herein attached so as to render the peptide immunogenic. Non-limiting examples of such carriers include proteins such as keyhole limpet hemocyanin (KLH), bovine serum albumin (BSA), ovalbumin (OVA), tetanus toxoid and human thyroglobulin. One function of the crosslinker is to introduce into the immunizing agent a spacer of sufficient size to prevent the carrier protein from masking the polypeptide. Suitable crosslinking agents are known in the art and are commercially available. The immunizing agent is then administered to a subject, such as a goat, sheep, rabbit, mouse, rat, guinea pig, pig, cow, buffalo or other appropriate non-human mammal in an amount sufficient to raise an immune response to the immunizing agent, specifically the polypeptide of SEQ ID NO: 2, 4, 5, 6 or 12 or any of the polypeptides disclosed in FIG. 4. The immunizing agent can be administered in combination with an adjuvant, such as Freund's Complete adjuvant, Freund's Incomplete adjuvant, aluminum salts, oil based adjuvants, saponins, chemically synthesized adjuvants, or other adjuvants.

Another embodiment provides for the use of the disclosed peptides for FMDV antigen or antibody detection. For example, the peptide can be used to coat an ELISA plate in a competitive or indirect ELISA format to detect FMDV antibody from diverse samples (e.g., natural or experimental infections). Alternatively, the peptide can be used in a liquid phase competitive ELISA for detection of FMDV antigen. In this example, an ELISA plate is coated with the 3ABC monoclonal antibody and a liquid sample containing the FMDV 3ABC antigen is then added and allowed to compete with a constant concentration of 3ABC peptide. Thus, one can detect 3ABC contaminants in vaccine preparations.

An example cELISA kit includes:
a) the antibodies or antigen binding fragments thereof optionally labeled with an enzyme or other label,
b) an immunoassay plate or other substrate coated with a polypeptide comprising an amino acid sequence selected from those disclosed in FIG. 4, SEQ ID NO: 3, SEQ ID NO: 4, SEQ ID NO: 5, SEQ ID NO: 6 and/or SEQ ID NO: 12,
c) if the antibody or antigen binding fragment thereof is not labeled with an enzyme or other label, an antibody against the antibody or antigen binding fragment thereof conjugated to an enzyme or label, and
d) reagents and tools for conducting the cELISA assay.

The antibody or antigen binding fragment thereof of the current disclosure provided in the kit can be chimeric antibodies, single chain antibodies, scFv antibodies, or Fab fragments. In one embodiment, the kit contains Mab 40C8 antibody as produced by hybridoma which is deposited with the American Type Culture Collection with Designation: PTA-122531.

The immunoassay plate can be coated with a polypeptide consisting essentially of the amino acid sequence selected from those disclosed in FIG. 4, SEQ ID NO: 2, SEQ ID NO:

3, SEQ ID NO: 4, SEQ ID NO: 5 and/or SEQ ID NO: 12 (or any combination thereof). Non-limiting examples of polypeptides that can be conjugated to the immunoassay plate include peptides consisting of those disclosed in FIG. 4, SEQ ID NO: 2, SEQ ID NO: 3, SEQ ID NO: 4, SEQ ID NO: 5 and/or SEQ ID NO: 12; 3ABC protein; or 3ABC protein carrying a mutation rendering it protease resistant (described in detail in the Materials and Methods section and the Examples below). Any peptide containing the epitopes for the antibodies or antigen binding fragments thereof disclosed herein can be used to coat the immunoassay plate and such embodiments are within the purview this disclosure.

The current disclosure also provides the following non-limiting embodiments:

1. An isolated antibody or antigen binding fragment thereof that specifically binds to 3ABC non-structural protein of Foot-and-Mouth Disease virus (FMDV), wherein the antibody or antigen binding fragment thereof specifically binds an epitope consisting essentially of SEQ ID NO: 3, SEQ ID NO: 4, SEQ ID NO: 5, SEQ ID NO: 6 or SEQ ID NO: 12.

2. The antibody or antigen binding fragment thereof of embodiment 1 that specifically binds the amino acid sequence of SEQ ID NO: 3, SEQ ID NO: 6, or SEQ ID NO: 12 as the epitope.

3. The antibody or antigen binding fragment thereof of embodiment 1 that specifically binds the amino acid sequence of SEQ ID NO: 4 as the epitope.

4. The antibody or antigen binding fragment thereof of embodiment 1 that specifically binds the amino acid sequence of SEQ ID NO: 5 as the epitope.

5. The antibody of embodiment 1, wherein the antibody is a monoclonal antibody.

6. The antibody of embodiment 1, wherein the antibody is a polyclonal antibody.

7. The antibody or antigen binding fragment thereof of embodiment 1, wherein the antibody is selected from a chimeric antibody, a single chain antibody, a single chain fragment variable (scFv) antibody, or a fragment antigen-binding (Fab fragment).

8. The antibody of embodiment 1, wherein the antibody is Mab 40C8 as produced by hybridoma which is deposited with the American Type Culture Collection with Designation: PTA-122531.

9. The antibody or antigen binding fragment thereof of embodiment 1, wherein the antibody or antigen binding fragment thereof is conjugated to a label.

10. The antibody of embodiment 9, wherein the label is selected from an enzyme label, a radioisotope, a fluorescent label, or a bioluminescent label.

11. A method of detecting FMDV infection in an animal, the method comprising contacting a sample from an animal with an antibody or antigen binding fragment thereof of that specifically binds to the 3ABC non-structural protein of FMDV, wherein the antibody or antigen binding fragment thereof specifically binds the amino acid sequence of SEQ ID NO: 2, SEQ ID NO: 3, SEQ ID NO: 4, SEQ ID NO: 5 SEQ ID NO: 6, or SEQ ID NO: 12.

12. The method of embodiment 11, wherein the sample obtained from the animal is a body-fluid sample or a tissue sample.

13. The method of embodiment 12, wherein the body-fluid sample is aqueous humor, vitreous humor, blood serum, blood plasma, cerebrospinal fluid, endolymph, perilymph, exudates, lymph, mucus, pericardial fluid, pleural fluid, synovial fluid, milk, or oral fluids.

14. The method of embodiment 12, wherein the tissue sample is brain, eyes, pineal gland, pituitary gland, thyroid gland, parathyroid glands, thorax, heart, lungs, esophagus, thymus gland, pleura, adrenal glands, appendix, gall bladder, urinary bladder, large intestine, small intestine, kidneys, liver, pancreas, spleen, stoma, prostate gland, testes, ovaries, or uterus.

15. The method of embodiment 11 or 12, wherein the assay is a Western blot analysis.

16. The method of embodiment 11 or 12, wherein the assay is an ELISA.

17. The method of embodiment 16, wherein the ELISA is sandwich ELISA, or competitive ELISA.

18. The method of embodiment 17, wherein the competitive ELISA is performed using an immunoassay plate, wherein the immunoassay plate is coated with one or more polypeptide consisting essentially of an amino acid sequence selected from SEQ ID NO: 2, SEQ ID NO: 3, SEQ ID NO: 4, SEQ ID NO: 5, SEQ ID NO: 6, or SEQ ID NO: 12.

19. The method of embodiment 16, wherein the antibody or antigen binding fragment thereof is conjugated to an enzyme.

20. The method of embodiment 19, wherein the enzyme is horseradish peroxidase.

21. The method of embodiment 11 or 12, wherein the antibody or antigen binding fragment thereof is conjugated to a label.

22. The method of embodiment 21, wherein the label is an enzyme label, a radioisotope, a fluorescent label, or a bioluminescent label.

23. A kit comprising an antibody or antigen binding fragment according to any one of embodiments 1-10, said antibody or antigen binding fragment specifically binding to 3ABC non-structural protein of FMDV, wherein the antibody or antigen binding fragment thereof specifically binds the amino acid sequence of SEQ ID NO: 2, SEQ ID NO: 3, SEQ ID NO: 4, SEQ ID NO: 5, SEQ ID NO: 6, or SEQ ID NO: 12.

24. The kit of embodiment 23, wherein said kit further comprising an immunoassay plate coated with a polypeptide comprising the amino acid sequence selected from SEQ ID NO: 2, SEQ ID NO: 3, SEQ ID NO: 4, SEQ ID NO: 5, SEQ ID NO: 6 or SEQ ID NO: 12, FMDV non-structural protein 3ABC or combinations thereof.

25. The kit of embodiment 23, wherein the antibody or antigen binding fragment thereof is conjugated to a label.

26. The kit of embodiment 23, wherein said label is an enzyme label, a radioisotope, a fluorescent label, or a bioluminescent label.

27. The kit of embodiment 23, wherein the antibody is a monoclonal antibody.

28. The kit of embodiment 23, wherein the antibody is a polyclonal antibody.

29. The kit of embodiment 23, wherein the antibody or antigen binding fragment thereof is a chimeric antibody, a single chain antibody, a scFv antibody, or a Fab fragment.

30. The kit of embodiment 23, wherein the antibody is Mab 40C8 as produced by hybridoma which is deposited with the American Type Culture Collection with Designation: PTA-122531.

31. A method of producing an antibody comprising immunizing an animal with an immunogen comprising a polypeptide consisting essentially of SEQ ID NO: 2, SEQ ID NO: 3, SEQ ID NO: 4, SEQ ID NO: 5, SEQ ID NO: 6 or SEQ ID NO: 12, or combinations thereof; and collecting antibodies from said animal.

32. The method according to embodiment 31, said method further comprising comparing the binding specificity of said collected antibodies to the monoclonal antibody 40C8.

33. The method of embodiment 31, said method comprising immunizing said animal, generating monoclonal antibodies from splenocytes isolated from said animal and comparing the binding specificity of monoclonal antibodies generated by said method with the 40C8 monoclonal antibody.

34. The method according to embodiment 32, wherein said generated monoclonal antibody specifically binds the amino acid sequence of SEQ ID NO: 3, SEQ ID NO: 4, SEQ ID NO: 5, SEQ ID NO: 6, or SEQ ID NO: 12 as the epitope.

35. The method according to embodiment 32, wherein said generated monoclonal antibody specifically binds the amino acid sequence of SEQ ID NO: 4 as the epitope.

36. The method according to embodiment 32, wherein said generated monoclonal antibody specifically binds the amino acid sequence of SEQ ID NO: 5 as the epitope.

37. A polypeptide consisting of an amino acid sequence selected from SEQ ID NO: 2, SEQ ID NO: 4, SEQ ID NO: 5, SEQ ID NO: 6 or SEQ ID NO: 12.

38. A polypeptide consisting essentially of an amino acid sequence selected from SEQ ID NO: 2, SEQ ID NO: 4, SEQ ID NO: 5, SEQ ID NO: 6 or SEQ ID NO: 12.

39. An immunogenic carrier protein covalently attached to:
a) a polypeptide consisting of an amino acid sequence selected from SEQ ID NO: 2, SEQ ID NO: 4, SEQ ID NO: 5, SEQ ID NO: 6 or SEQ ID NO: 12; or
b) consisting essentially of an amino acid sequence selected from SEQ ID NO: 2, SEQ ID NO: 4, SEQ ID NO: 5, SEQ ID NO: 6 or SEQ ID NO: 12.

40. A composition of matter comprising a polypeptide bound to a substrate, said polypeptide:
a) consisting of an amino acid sequence selected from SEQ ID NO: 2, SEQ ID NO: 4, SEQ ID NO: 5, SEQ ID NO: 6 or SEQ ID NO: 12; or
b) consisting essentially of an amino acid sequence selected from SEQ ID NO: 2, SEQ ID NO: 4, SEQ ID NO: 5, SEQ ID NO: 6 or SEQ ID NO: 12.

41. A composition of matter comprising a substrate to which an antibody according ant one of embodiments 1-10 is bound.

42. The method of any one of embodiments 11-22, wherein said antibody binds to the same epitope as the 40C8 antibody.

43. The method of embodiment 42, wherein said antibody is the antibody produced by the hybridoma 40C8 or is an antigen binding fragment thereof.

44. An immunogenic composition comprising an adjuvant and a polypeptide:
a) consisting of an amino acid sequence selected from SEQ ID NO: 2, SEQ ID NO: 4, SEQ ID NO: 5, SEQ ID NO: 6 or SEQ ID NO: 12; or
b) consisting essentially of an amino acid sequence selected from SEQ ID NO: 2, SEQ ID NO: 4, SEQ ID NO: 5, SEQ ID NO: 6 or SEQ ID NO: 12, said polypeptide being, optionally, conjugated to an immunogenic carrier protein.

45. The method of embodiment 11 or 12, wherein the sample is from a vaccinated animal, infected animal or a combination of vaccinated and infected animals.

46. The method of embodiments 11, 12, 17-22 or 45, wherein said method is a competitive immunoassay and said method comprises:
combining said biological sample with Mab 40C8 or an antigen binding fragment thereof, or antibodies having the binding specificity of Mab 40C8, or antigen binding fragments thereof, prior to contacting said biological with one or more 3ABC polypeptide or one or more polypeptide comprising an epitope comprising SEQ ID NO: 3, SEQ ID NO: 4, SEQ ID NO: 5, SEQ ID NO: 6 or SEQ ID NO: 12 or a 3ABC polypeptide;
contacting an immunoassay plate coated with one or more 3ABC polypeptide or one or more polypeptide containing an epitope consisting essentially of an amino acid sequence selected from SEQ ID NO: 3, SEQ ID NO: 4, SEQ ID NO: 5, SEQ ID NO: 6 or SEQ ID NO: 12 with an antibody or antigen binding fragment having the binding specificity of Mab 40C8, optionally washing said plate and, subsequently contacting said immunoassay plate with said biological sample; or
contacting an immunoassay plate coated with one or more 3ABC polypeptide or one or more polypeptide containing an epitope consisting essentially of an amino acid sequence selected from SEQ ID NO: 3, SEQ ID NO: 4, SEQ ID NO: 5, SEQ ID NO: 6 or SEQ ID NO: 12 with said biological sample, optionally washing said plate and, subsequently contacting said immunoassay plate with an antibody or antigen binding fragment having the binding specificity of Mab 40C8.

47. The method of embodiment 46, wherein said polypeptide comprises FMDV 3ABC.

48. The method of embodiment 46, wherein said method comprises contacting an immunoassay plate coated with one or more 3ABC polypeptide or one or more polypeptide containing an epitope consisting essentially of an amino acid sequence selected from SEQ ID NO: 3, SEQ ID NO: 4, SEQ ID NO: 5, SEQ ID NO: 6 or SEQ ID NO: 12 with an antibody or antigen binding fragment having the binding specificity of Mab 40C8, optionally washing said plate and, subsequently contacting said immunoassay plate with said biological samples, infected animals being identified by reduced binding of antibodies in said biological sample to said polypeptide being the inhibition of antibody binding.

49. The method of embodiment 46, wherein said method comprises contacting an immunoassay plate coated with one or more 3ABC polypeptide or one or more polypeptide containing an epitope consisting essentially of an amino acid sequence selected from SEQ ID NO: 3, SEQ ID NO: 4, SEQ ID NO: 5, SEQ ID NO: 6 or SEQ ID NO: 12 with said biological sample; contacting said immunoassay plate with an antibody or antigen binding fragment having the binding specificity of Mab 40C8 that is labeled with at least one of a fluorescent label, an enzymatic label or a radiolabel; and detecting the binding of said labeled antibody or antigen.

50. The method of embodiment 49, wherein reduced binding of said labeled antibody indicates that the animal from which the biological sample was obtained is infected by FMDV.

EXAMPLE MATERIALS AND METHODS

Example: Cloning and Expression of 3ABC* His-Tagged Recombinant Protein from *E. coli* Expression Plasmid The viral RNA for the FMDV O1 Campos strain was isolated from FMDV infected BHK-21 cells following manufacturer protocols (RNeasy kit, Qiagen, Valencia, Calif.). The required recombinant protein 3ABC* fragment of the viral genome was transcribed to cDNA using SuperScript™ III First-Strand Synthesis System for real-time polymerase chain reaction (RT-PCR) (Invitrogen, Carlsbad, Calif.) following the manufacturer's instructions. The cDNA obtained was then amplified by an overlap extension PCR (Forward oligonucleotide: 5'-CAATTCCTTC-CCAAAAATCT-3' (SEQ ID NO: 7), Reverse oligonucleotide: 5'-GTGGTGTGGTTCGGGGTCCAA-3' (SEQ ID NO: 8). Expected PCR product size was 1316 bp). Site-directed mutagenesis and overlapping PCR was used to introduce a mutation (*) that changes the residue Cysteine at position 163 into an Arginine at the active site of the $3C_{pro}$ viral proteinase.

Figure 8:
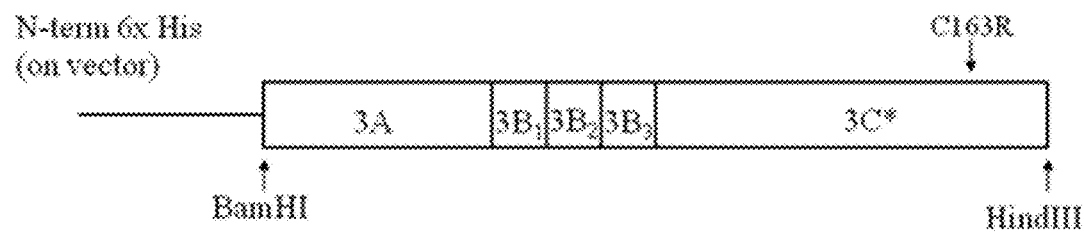
FIG. 8 shows schematic of recombinant 3ABC* protein (* indicates mutation in the protein).
Figure 9:
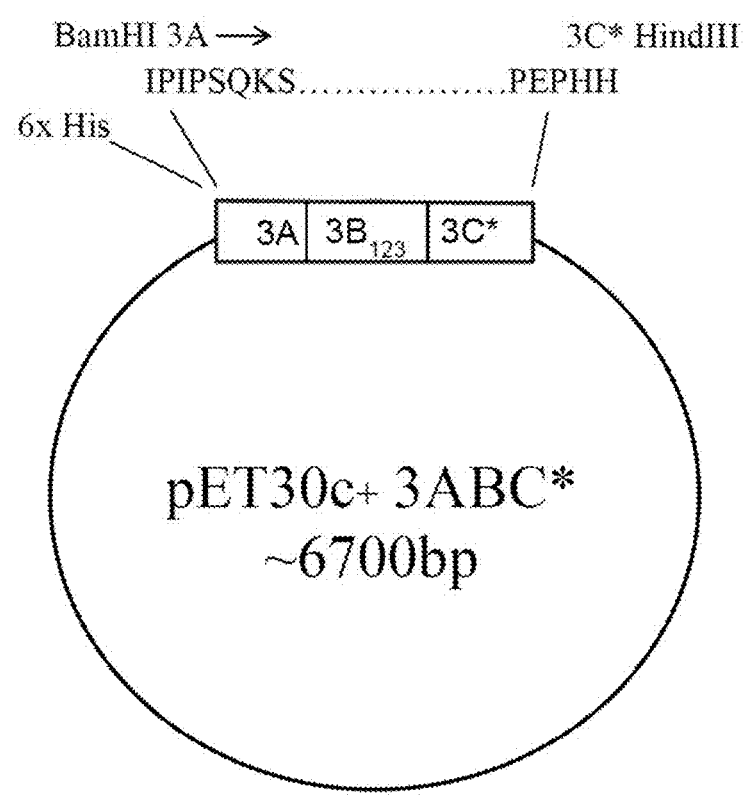
FIG. 9 shows schematic representation of entire plasmid for the expression of FMDV O1 Campos mutant 3ABC* protein (SEQ ID NO: 29 and SEQ ID NO: 30).

The schematic representations of the recombinant protein and of the plasmid used for expression in prokaryotic cells are shown in FIG. 8 and FIG. 9. The sense and antisense primers were designed for cloning of 3ABC* PCR into pET30c 6×His tag expression plasmid containing a 6×His-tag at the N-terminus of the cloned protein. Cloning of the 3ABC* insert was accomplished by BamHI/HindIII restriction endonuclease digestion using standard molecular biology techniques. Sequence analysis verified the presence of the correct mutant recombinant protein. This was accomplished by using Big Dye Terminator Cycle Sequencing Kits (Applied Biosystems, Foster City, Calif.) and a PRISM 3700 automated sequencer.

p3ABC* was expressed in *E. coli* Rosetta (DE3)pLysS competent cells and induced with addition of isopropyl β-D-1-thiogalactopyranoside (IPTG) as follows:

Expression:
1. Grow single colony in 5 ml LB broth containing 0.4% glucose and 50 μg/ml kanamycin and 20 μg/ml chloramphenicol, overnight at 37° C. and 220 rpm in an incubator.
2. Inoculate the starter culture to 50 ml LB broth containing identical antibiotic concentration.
3. Grow cells at 37° C. and 220 rpm in the incubator to reach OD=0.8.
4. Induce with 1 mM IPTG (final concentration); grow at 37° C. for 4 hrs.
5. Freeze the cell pellet in −20° C. freezer.

Solubilization:
1. Thaw the frozen cell pellet on ice for 30 min.
2. Resuspend the cell pellet in BugBuster® reagent (5 ml buffer/g cells) (EMD Millipore, Billerica, Mass.).
3. Add Benzonase (Novagen, Bilerica, Mass.), lysozyme, leupeptin, and pepstatin to 1× concentration.
4. Incubate at room temperature for 20 min with intermittent stirring.
5. Centrifuge at 11,600 rpm in a SL-50T rotor for 20 minutes at 4° C. Discard supernatant.
6. Add same amount of volume (as above) of 1:10 Bugbuster®.
7. Centrifuge at 3000 rpm in a ST-H750 rotor for 20 min at 4° C.
8. Collect the pellet and resuspend in 1:10 concentration of BugBuster® again.
9. Centrifuge at 3000 rpm using ST-H750 rotor for 20 min at 4° C.
10. Resuspend the pellet in 1:10 Bugbuster® and centrifuge at 11,600 rpm for 20 min at 4° C. Discard the supernatant.
11. The protein was harvested from inclusion bodies and the protein pellet was solubilized with 100 mM $NaH_2PO_4$, 10 mM Tris, 8 M Urea pH 8 supplemented with 12 mM β-mercaptoethanol (BME) and 10% glycerol for 1 hour on ice.
12. The protein solution was centrifuged at 11,600 rpm in a SL-50T rotor for 20 min at 4° C. The supernatant was collected.

Figure 10:
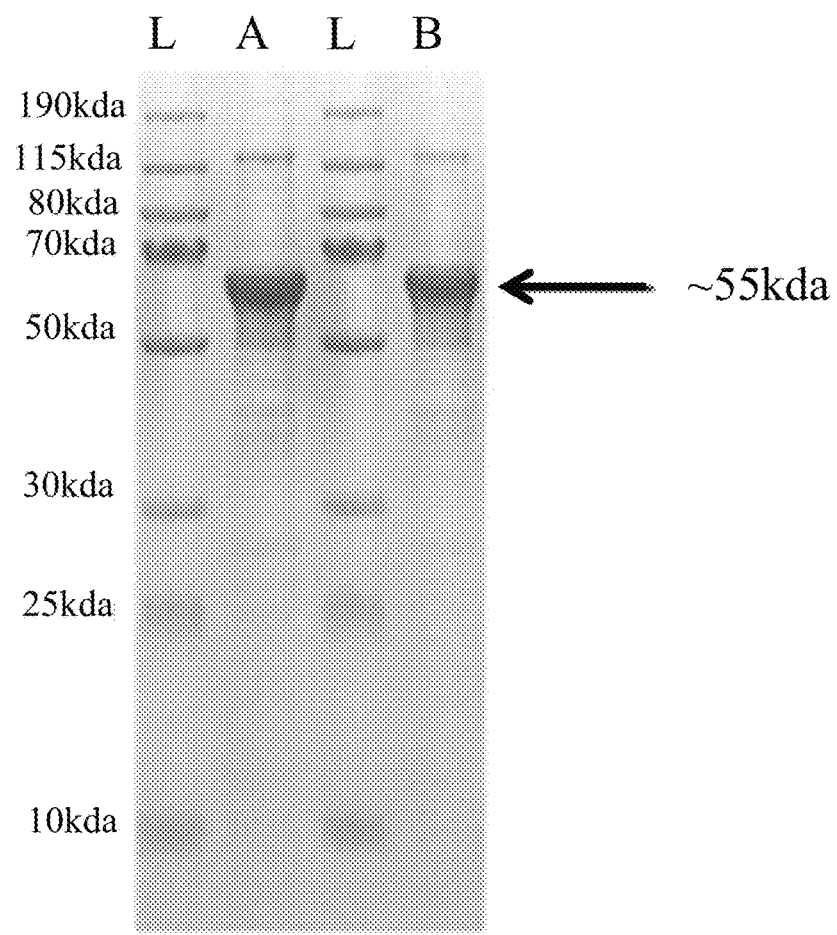
FIG. 10 shows SDS PAGE gel of recombinant 3ABC* protein. L: molecular weight markers; A: lot A; B: lot B.

Protein preparations were aliquoted as 100 μl and stored at −20° C. Two lots of 3ABC* were verified in 12% Bis-Tris sodium dodecyl sulfate polyacrylamide gel electrophoresis (SDS PAGE) gel (FIG. 10) and can be seen as an approximate 55 kDa band.

A standard BCA protein assay (Thermo Fisher Scientific Inc., Waltham, Mass.) was performed to determine the approximate concentration of the crude recombinant protein preparation. Table 2 shows the concentration and inventory of the two lots of recombinant proteins.

TABLE 2

| Batch information of recombinant 3ABC* proteins | |
|---|---|
| Recombinant protein | Concentration (mg/ml) |
| FMDV 3ABC* Lot 20112A | 7.5 |
| FMDV 3ABC* Lot 20112B | 6.25 |

Following are examples which illustrate procedures for practicing the invention. These examples should not be construed as limiting. All percentages are by weight and all solvent mixture proportions are by volume unless otherwise noted.

Example 1—Mab 40C8 Production

An embodiment of the current disclosure provides a cELISA that utilizes an indicator monoclonal antibody (Mab), Mab 40C8, in a competitive format, i.e. sera from infected animals are used to block the binding of the indicator antibody to a target antigen. Mab 40C8 specifically binds to a B-cell linear epitope NH2-GPYAGPLERQK-PLK—COOH (SEQ ID NO: 3) of the 3ABC protein of foot-and-mouth disease virus (FMDV) and is a key component of the cELISA. The minimal optimal reactive epitope is mapped to GPLERQ (SEQ ID NO: 4), enabling unique and useful function of the Mab in diagnostic testing that are described here after.

Figure 3:
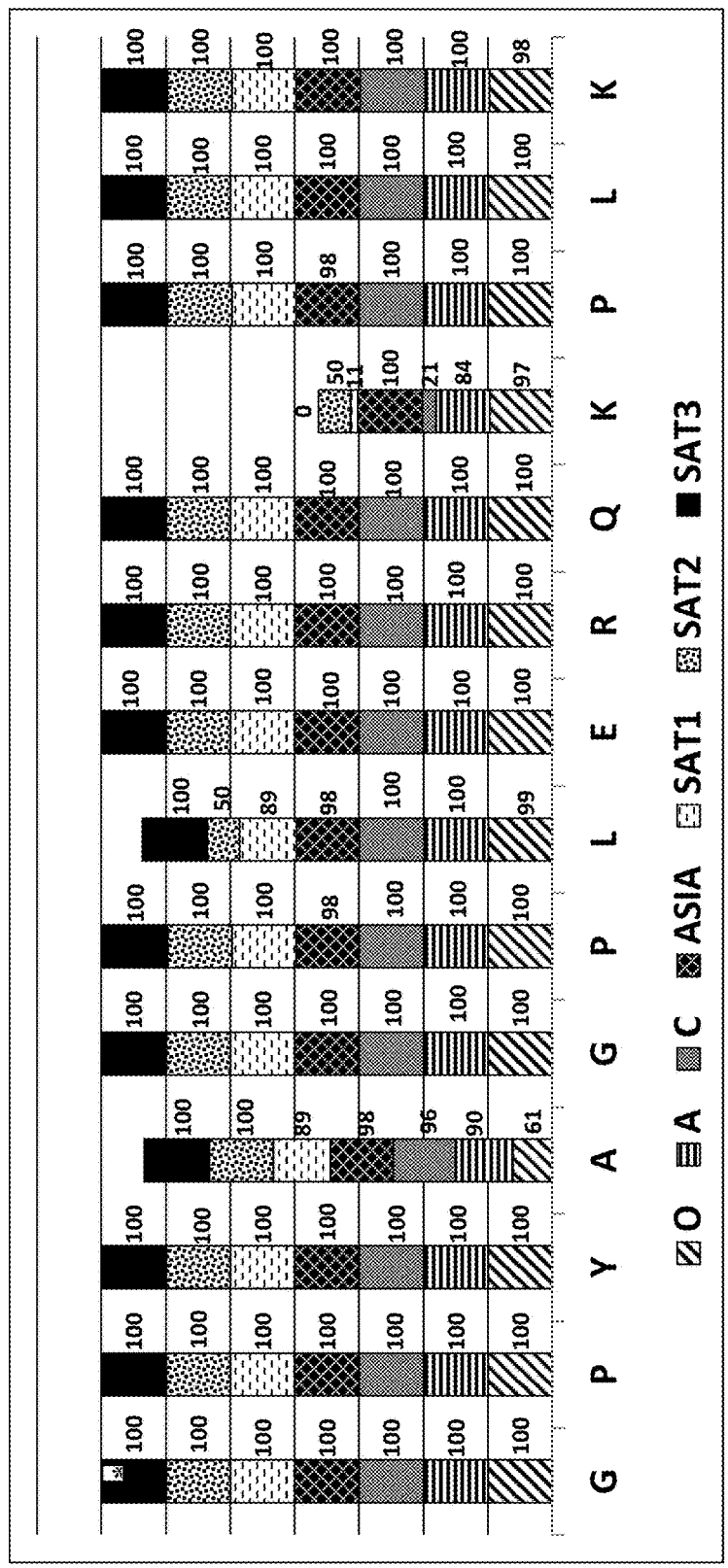
FIG. 3 shows amino acid variability within the 3ABC peptide; the variability is higher in residues alanine (A), leucine (L) and lysine (K) at positions 4, 7, and 11, respectively.

Mab 40C8 was generated using the peptide NH2-CGPY-AGPLERQKPLK—COOH, (SEQ ID NO: 6, FIG. 1, which was chemically synthesized and purified by HPLC. Sequence analysis (n=331 strains available in GenBank), indicates ~20% genetic variability in this epitope (FIG. 2) indicating that a monoclonal generated against this peptide may recognize these sequence variants, thus enabling a cross-reactive serological test. The variability within the peptide is higher in the amino acid residues alanine (A), leucine (L), and lysine (K) at position 4, 7 and 11, respectively (FIG. 3).

The peptide was conjugated to KLH and used for mice immunization and Mab production using standard protocols. Briefly, female BALB/C mice were immunized subcutaneously with 20 μg of the peptide NH2-GPYAGPLERQK-PLK—COOH (SEQ ID NO: 3) conjugated to KLH emulsified in an equal volume of Complete Freund's Adjuvant. Three identical boosters emulsified in incomplete Freund's adjuvant were given at four weeks interval. The mice were boosted with the peptide-KLH conjugate in PBS (40 μg/mouse) by intraperitoneal injection 4 days before fusion. Immunized spleen cells were fused with myeloma cells (P3X63 Ag8.653). After 2 weeks, hybridoma supernatants were screened using the FMDV recombinant 3ABC as the antigen in an indirect ELISA. Mab 40C8 exhibited strong reactivity with the 3ABC antigen and was characterized as IgG1 isotype with kappa light chains.

Mab 40C8 Reactivity to Peptides and 3ABC Recombinant Protein

Additional indirect ELISA testing confirmed reactivity to diverse 3ABC peptide variants (FIG. 4). This result indicates that this Mab exhibits broad peptide reactivity, potentially enabling detection of diverse strains of FMDV (n=331 by in silico analysis, as depicted in FIG. 2). The minimal epitopes are GPLERQ (SEQ ID NO: 4), and residues 2 and 3 of this sequence are not critical for Mab 40C8 binding.

Figure 5:
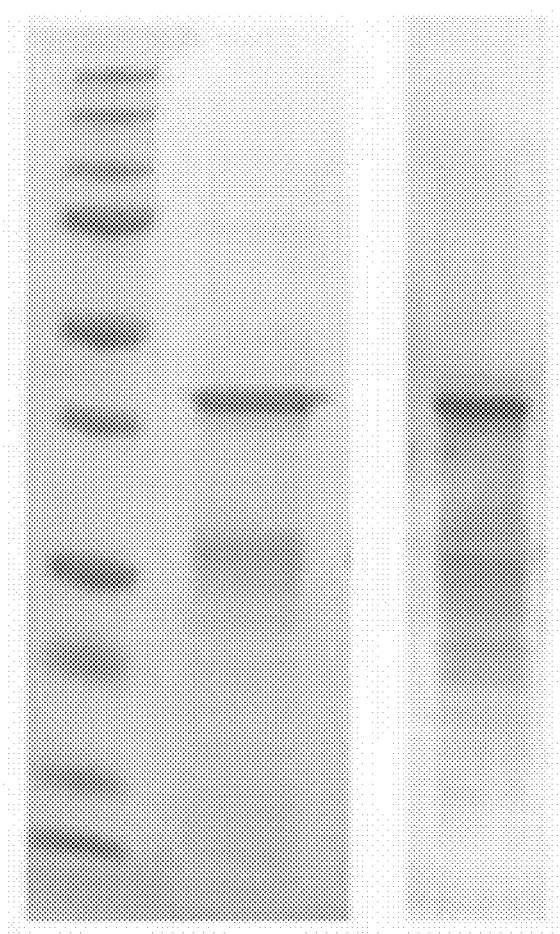
FIG. 5 shows that Mab 40C8 exhibited positive reactivity to the 3ABC recombinant protein, PET31b3b12X (44.7 kDa; SEQ ID NO: 2), which contains sequence variations within the 3B portion of the protein. Left: intact recombinant protein, analyzed by SDS PAGE; Right: specific Mab 40C8 detection of recombinant protein using Western blot analysis.

Mab 40C8 also exhibited strong Western blot reactivity to the 3ABC recombinant protein, consisting of all sequence variants within the 3ABC epitope (FIG. 5). Furthermore, this Mab was able to compete with sera from a FMDV infected animals to the recombinant 3ABC protein, demonstrating the feasibility of a competitive ELISA application.

Mab 40C8 Reactivity to the Six FMDV Serotypes Infected Cell Lysates

Figure 6:
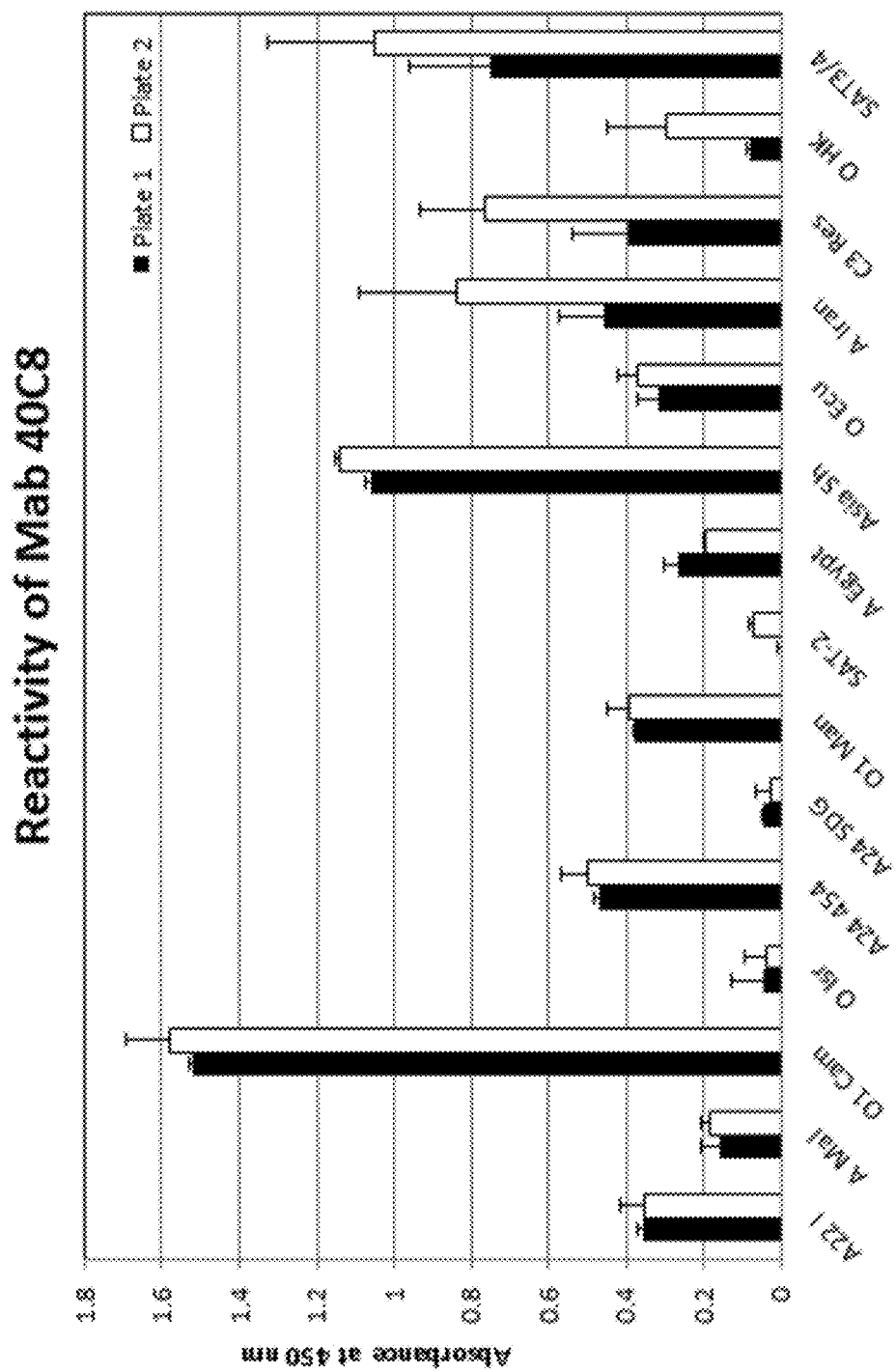
FIG. 6 shows reactivity of Mab 40C8-HRP with 6 major FMDV serotypes tested in direct ELISA.

For a cELISA, Mab 40C8 was directly conjugated to the horseradish peroxidase (HRP) detection system and the reactivity of Mab 40C8 conjugated to HRP (40C8-HRP) was screened with a panel of fifteen FMDV isolates using a direct ELISA format. These FMDV antigens were prepared from a cell line known to be highly permissive to FMDV growth (LFBK αvβ6). FIG. 6 shows that in two separate experiments 40C8-HRP bound to FMDV antigen in infected cell lysates. Variability in binding (e.g., measured by 450 nm absorbance) can be attributed to differences in the FMDV antigen content in the cell lysates. For example, isolates such as serotype O Israel (O Isr), A24 Cruzeiro SDG (A24 SDG), and SAT-2 that did not bind efficiently to Mab 40C8 in this assay were suspected of not growing well since other isolates of the same serotype and strain were reactive to Mab 40C8 using Western Blot analysis (see FIG. 7 and associated result descriptions below). Moreover, a similar low immunoreactivity for O Isr and A24 SDG was observed in another experiment (data not shown) in which the pan-FMDV specific monoclonal antibody, F1412SA (F14), which specifically binds an epitope in the FMDV VP2 (1B) protein, was used as a positive control. Collectively, these ELISA results indicate that Mab 40C8 exhibited reactivity to six FMDV serotypes using cell-lysates. SAT-1, the seventh serotype, was not available at the time of this analysis.

Furthermore, Western blot analysis was also performed to verify the ELISA results. Cell lysates prepared from BHK-21 cells infected with FMD viruses representing different serotypes were mixed with 2× Laemmli buffer, boiled, and stored. For Western blot analysis, a 1/10 fraction of cell extracts was run on 12% SDS-PAGE gels and transferred onto nitrocellulose blots following standard procedures. The blots were probed using Mab 40C8. The results are shown in FIGS. 7A and 7B. As a control, and to demonstrate that all samples contained the viral antigen, a second Western blot was developed using a FMDV 3D-specific monoclonal antibody (see upper panel in FIG. 5A where a product of about 52 KDa is detected that corresponds to the FMDV protein 3D). Together these results show that Mab 40C8 reacted with FMDV 3ABC across six strains in four serotypes. Certain strains exhibit strong reactivity while others required higher concentration of the Mab 40C8. The collective ELISA and Western blot data demonstrate that Mab 40C8 specifically binds FMDV proteins from all available serotypes.

SAT-2 Reactivity Confirmation

In the initial studies, characterizing the reactivity of the Mab 40C8 with cell culture-grown FMDV serotype SAT-2, results indicated that one strain of SAT-2 was not reactive, as seen in FIG. 6, and FIG. 7B. However, when another SAT-2 strain was used, there was a positive reaction (FIG. 7A). In additional studies using different strains of SAT-2 in which animals were infected, all three serum samples were positive. So, it appears that the one strain of SAT-2 was not reactive due to low cell culture growth.

Mab 40C8 Non Reactivity to Ad-FMD Vaccines Infected Cells

The current disclosure provides a cELISA that can also discriminate between animals infected with FMDV and those immunized with FMD vaccines that have been inactivated and purified of NSPs. The FMD vaccine immunized animals (immunized using inactivated, purified FMDV vaccine or an adenovector serotype 5 vaccine) do not contain FMDV protein 3ABC which is recognized by Mab 40C8-HRP. For example, a vaccine containing the molecular clone of the adenovector serotype 5 carrying the FMDV capsid and processing genes (Ad-FMD) lack the specific 3ABC immunogenic site in the FMDV 3ABC protein. The antibody responses of animals immunized with vaccines lacking the viral non-structural proteins (e.g. Ad-FMD or inactivated, purified FMDV vaccines) can be discriminated or differentiated from those responses exhibited by FMDV infected animals. These differences can be detected by companion diagnostic tests, so-called DIVA (differentiation between infected and vaccinated animals). The Ad-FMD vaccines were designed to be vaccines with DIVA capabilities using a FMDV 3ABC cELISA designed as a companion diagnostic assay. The reactivity of Mab 40C8 with Ad-FMD infected cells was screened with FMDV Asia 1, O1 Campos, and O1 Manisa constructs using a direct ELISA as above. Ad-FMD-infected M2A cells actively express FMDV capsid and some processing genes. Ad-FMD antigens (infected M2A cell lysates) were directly adsorbed to ELISA plates and processed as above. Table 3 shows the clear binding of Mab F14 to the expressed FMDV capsid proteins, and the lack of binding of Mab 40C8 to the Ad-FMD cell lysates that lack immunogenic FMDV 3ABC nonstructural proteins. Therefore, the ELISA of the present disclosure can serve as a companion diagnostic assay for Ad-FMD vaccines.

TABLE 3

Immunoreactivity of Mab 40C8 and Mab F14 to Ad-FMD vaccine constructs grown in M2A cells.

| Adenovector FMD vaccine construct | Highest dilution for a positive response | |
|---|---|---|
| | Mab 40C8 | Mab F14 |
| Ad5-ASaudi Arabia 95 | <1:2* | >1:64 |
| Ad5-O1 Manisa | <1:2 | >1:64 |
| Ad5-O1 Campos | <1:2 | >1:64 |
| Ad5-O1Campos.2B | <1:2 | >1:64 |
| Ad5-O1Campos.2B + F(RGD) | <1:2 | >1:64 |
| M2A cells (no vaccine control) | <1:2 | <1:2 |

*No positive reaction detected at the lowest dilution tested (1:2)

Example 2—3ABC cELISA Kit

Preparation of Horse-Radish Peroxidase (HRPO)-Conjugated Mab 40C8

Mab 40C8 ascites purified by sodium ammonium sulfate cut method were diluted in PBS to provide 2 mg/ml antibody. Mab 40C8 was dialyzed against 0.1 M sodium bicarbonate/carbonate buffer, pH 9.6. Half ml of a 4 mg/ml horseradish peroxidase solution (HRPO) dissolved in distilled water was mixed with 100 μl of freshly prepared 0.1

M sodium periodate by stirring for 20 minutes at room temperature. The HRPO/sodium periodate solution was dialyzed against 1.0 mM sodium acetate buffer, pH 4.4 at 4° C. The pH of HRPO/sodium periodate solution was adjusted from 4.05 to pH 9.6 by adding 15 µl of freshly prepared 0.1 M sodium carbonate. The dialyzed Mab were combined with the HRPO/sodium periodate solution, and stirred for 2 hours at room temperature. Fifty µl of freshly prepared 4 mg/ml sodium borohydride solution was slowly added to the HRPO/FMDV ascites SAS Cut solution, incubated for 2 hours at 4° C., and then dialyzed against 1×PBS. The HRPO-conjugated Mab 40C8 was stabilized by adding a final concentration of 10% heat inactivated goat serum, 0.01% thimerosal, and 0.03% WAWA (4-aminoantipyrine).

Example: Preparation of Recombinant 3ABC-Coated Immunoassay Plate

A dilution of recombinant 3ABC was made in 0.1 M carbonate/bicarbonate buffer. Immunoassay plates were filled with 50 µl antigen per well, incubated in humid chamber overnight at 4° C. Wells were blocked with 20 µl blocking agent by incubating for 2 hours at 37° C. in humid chamber. The plates were dried overnight after discarding the liquid.

Example: Optimizations of Other Format Variables and Formulation of Kit Components Other format variables including serum dilution factor, serum incubation time, buffer types for serum dilution, conjugate dilution buffer and plate wash were thoroughly compared and the combination supporting best analytical sensitivity and specificity was chosen. Components of the kit were formulated as follows.
1. Test serum dilution: PBS
2. Serum dilution factor: 1:2
3. Conjugate diluting buffer: 1:2 dilution of Stabilzyme (SurModics, Inc., Eden Prairie, Minn.) in PBS
4. Wash buffer: PBS containing 0.1% TWEEN (polysorbate 20)
5. Color reaction substrate: TMB (3,3',5,5'-Tetramethylbenzidine)

Preparation of Positive and Negative Controls

FMDV antibody negative bovine and porcine from FMDV-free farms in the U.S. were screened using a 3ABC cELISA. One bovine and three porcine were first immunized with recombinant 3ABC emulsified in Complete Freund's Adjuvant and then boosted with the same antigen emulsified in Incomplete Freund's Adjuvant. Serum from a FMDV negative bovine was used as the negative control in the assay. Positive bovine and porcine control serum was also collected and used to validate the immunoassay. These non-infectious positive controls showed reliable and concentration-dependent positive results in the cELISA format (Table 4).

Example: Assay Procedure

1. Add 50 µl serum at 1:2 in PBS to each well and incubate 30 min at room temperature.
2. Wash plate three times with 250 µl per well.
3. Add 50 µl HRP conjugated Mab and incubate at room temperature for 30 min.
4. Wash plate 3 times with 250 µl per well wash buffer.
5. Add 50 µl substrate per well and incubate 20 min at room temperature.
6. Add 50 µl Stop solution to each well and read at 450 nm.

TABLE 4

Representative QC data tested with sensitivity panel and control sera (bovine positive and negative)

| Sample I.D., Dilution | OD | OD | Mean | % Inhibition |
|---|---|---|---|---|
| C673 (+), 1:20 | 0.204 | 0.198 | 0.201 | 77.4 |
| C673 (+), 1:40 | 0.274 | 0.278 | 0.276 | 68.9 |
| C673 (+), 1:80 | 0.392 | 0.393 | 0.393 | 55.8 |
| C673 (+), 1:160 | 0.602 | 0.598 | 0.600 | 32.5 |
| Kit (−) | 0.905 | 0.924 | 0.889 | 0.0 |
|  | 0.849 | 0.876 |  |  |
| Kit (+) | 0.265 | 0.266 | 0.259 | 70.8 |
|  | 0.250 | 0.256 |  |  |

Example: Analytical Sensitivity Evaluation

Seven FMDV Serotypes Limit of Detection Analysis

In order to determine the analytical sensitivity of the assay, sera collected from animals infected with one of each of the seven FMDV serotypes were diluted two-fold, to a maximum dilution of 1:2048. Samples from each dilution were evaluated in the 3ABC ELISA twice and once in a commercially available assay according to manufacturer's instructions (PrioCHECK® FMDV NS Antibody ELISA, ThermoFisher Scientific, Grand Island, N.Y.). The highest dilution at which a positive reaction was recorded is listed in Table 5. The analytical sensitivity for the 3ABC ELISA was at least 16- to 32-fold more sensitive for the Asia-1 serotype sample (cut-off dependent), two-fold more sensitive for serotype O 1, comparable sensitivity for serotypes A, C, SAT-1, and SAT-2, and one dilution less sensitive for SAT-3 compared to the PrioCHECK® FMDV NS Antibody ELISA. Sera collected from animals infected with one of the seven FMDV serotypes were reactive in both assays, and the sensitivity for the 3ABC ELISA was optimal for a competitive ELISA format.

TABLE 5

Analytical Sensitivity of the 3ABC ELISA for seven FMDV serotypes with 35% inhibition as the cut-off (1st test) (45% inhibition as the cut-off in the 2nd test). For example, 1:2048 detection is better/more sensitive than 1:32.

| | Highest dilution for a positive response | | |
|---|---|---|---|
| FMDV serotype | 3ABC ELISA (1st test) | 3ABC ELISA (2nd test) | PrioCHECK ® |
| A | 1:512 (256) | 1:256 (128) | 1:128 |
| Asia-1 | 1:2048 (512) | 1:2048 (1024) | 1:32 |
| C | 1:64 (32) | 1:128 (32) | 1:32 |
| O 1 | 1:512 (256) | 1:256 (128) | 1:64 |
| SAT-1 | 1:512 (256) | 1:256 (128) | 1:128 |
| SAT-2 | 1:128 (64) | 1:64 (64) | 1:32 |
| SAT-3 | 1:32 (16) | 1:32 (16) | 1:32 |

Post-Infection Antibody Detection Time Point/Window Determination

One male castrated steer was infected intradermolingually (IDL) with one FMDV serotype, (4 calves were each infected with one of 4 FMDV serotypes, A Iraq 2009, Asia 1 Shamir, SAT-1, and O Israel 2008). For each IDL-challenge calf, four uninfected cattle were mingled in order to be infected via the contact route. Serum samples were collected from each animal nearly every day from days 0 to 14, and then on days 21 or 22, 28, and 35 or 36.

Figure 11:
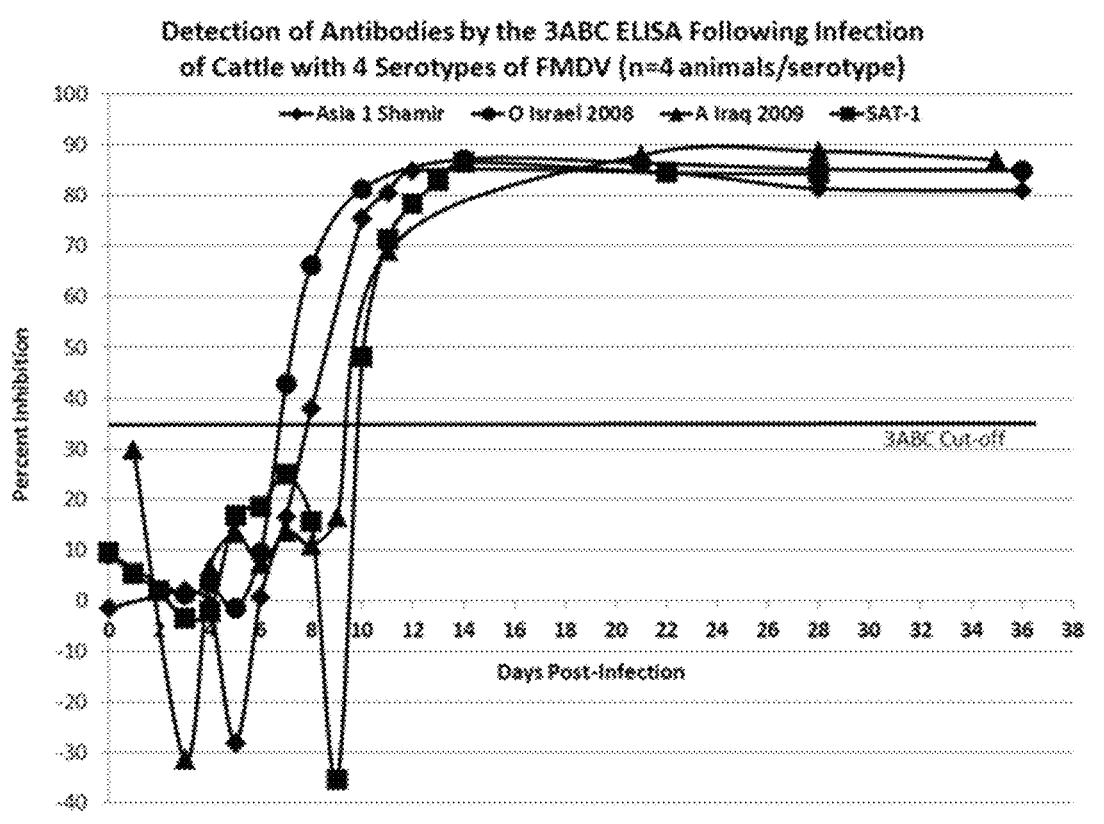

The 3ABC ELISA detected antibodies in sera from cattle infected with one of the four FMDV serotypes between 7 to 10 days post-infection (dpi) (FIG. 11). Antibodies to FMDV O Israel 2008 were detected by 7 dpi, to Asia 1 Shamir by 8 dpi, to A Iraq 2009 by 9 dpi, and to SAT-1 by 10 dpi.

In another embodiment designed to determine when antibodies to the FMDV 3ABC nonstructural proteins can be detected by the 3ABC ELISA following infection, sera were collected over time from cattle that were infected with one of three FMDV serotypes, SAT-1, SAT-2, or SAT-3. Sera from various days post-infection (dpi) were evaluated using the 3ABC ELISA. The first day on which there was a positive reaction in the 3ABC ELISA are summarized in Table 6.

TABLE 6

Detection of antibodies to FMDV nonstructural proteins from FMDV-infected cattle.

| Test used to detect antibodies to FMDV non-structural proteins | Days Post-Infection when antibodies to FMDV non-structural proteins were detected in cattle sera following infection with one of three FMDV serotypes (no. cattle) | | |
|---|---|---|---|
| | SAT-1 (n = 2) | SAT-2 (n = 2) | SAT-3 (n = 2) |
| 3ABC ELISA | 7, 10 | 6, 4 | 10, 11 |

These data indicates that the new FMDV 3ABC ELISA will be useful in detecting antibodies in cattle within 7 to 13 days post-infection with any one of the FMDV serotype SAT 1, SAT-2, or SAT-3 strains.

Example: Analytical Specificity Evaluation

FMD Look-Alike Samples Specificity Analysis

Diagnostic bovine sera samples previously evaluated and identified as having been collected from animals infected with pathogens that cause FMD look-alike lesions were tested with the 3ABC ELISA, the FMDV 3D virus infection associated antigen agar gel immunodiffusion (VIAA AGID), and by assays specific for the pathogen, e.g. Vesicular Stomatitis Virus (VSV) ELISA. Data are summarized in Table 7.

TABLE 7

Specificity of FMDV 3ABC ELISA on diagnostic serum samples that were confirmed as negative for FMDV antibodies and positive for VSV antibodies.

| No. of samples tested | No. Identified as Positive | | | Specificity |
|---|---|---|---|---|
| | VSV ELISA | FMDV 3D VIAA AGID | FMDV 3ABC ELISA | |
| 55 | 55 | 0 | 0 | 100% |

The specificity was 100% for sera tested from 55 cattle that had been infected with VSV and were positive for VSV antibodies. In the 3ABC ELISA, all samples exhibited ≤28% inhibition with an average of −12% inhibition and a standard deviation of 25%.

In another experiment, 44 samples from 8 species of FMDV-susceptible animals that exhibited vesicular lesions but were free of FMDV, were tested by three assays: 1) FMDV 3ABC ELISA, 2) FMDV 3D VIAA AGID, and 3) FMDV PrioCHECK. Data are summarized in Table 8.

TABLE 8

Specificity of FMDV 3ABC ELISA on sera from vesicular disease diagnostic samples that were confirmed as FMDV negative

| Animal Species | No. Identified as Negative | | | No. Identified As Positive by any of the three assays |
|---|---|---|---|---|
| | FMDV 3ABC ELISA | FMDV 3D VIAA AGID | FMDV PrioCHECK ® | |
| Alpaca | 2 | 2 | 2 | 0 |
| Bison | 1 | 1 | 1 | 0 |
| Bovine | 28 | 28 | 28 | 0 |
| Buffalo | 1 | 1 | 1 | 0 |
| Goat | 4 | 4 | 4 | 0 |
| Ovine | 2 | 2 | 2 | 0 |
| Swine | 4 | 4 | 4 | 0 |
| Yak | 2 | 2 | 2 | 0 |
| Total | 44 | 44 | 44 | 0 |

The specificity of the 3ABC ELISA was 100% for 44 samples collected from 8 species of animals that were FMDV free and exhibited vesicular lesions, i.e. rule-out data provided by the USDA Animal and Plant Health Inspection Service Foreign Animal Disease Diagnostic Laboratory. The same results were obtained in the FMDV PrioCHECK® FMDV NS Antibody ELISA and the FMDV 3D VIAA AGID assays.

Adenovirus-A24 FMD Vaccine Vaccinated Samples Specificity Analysis

Figure 12:
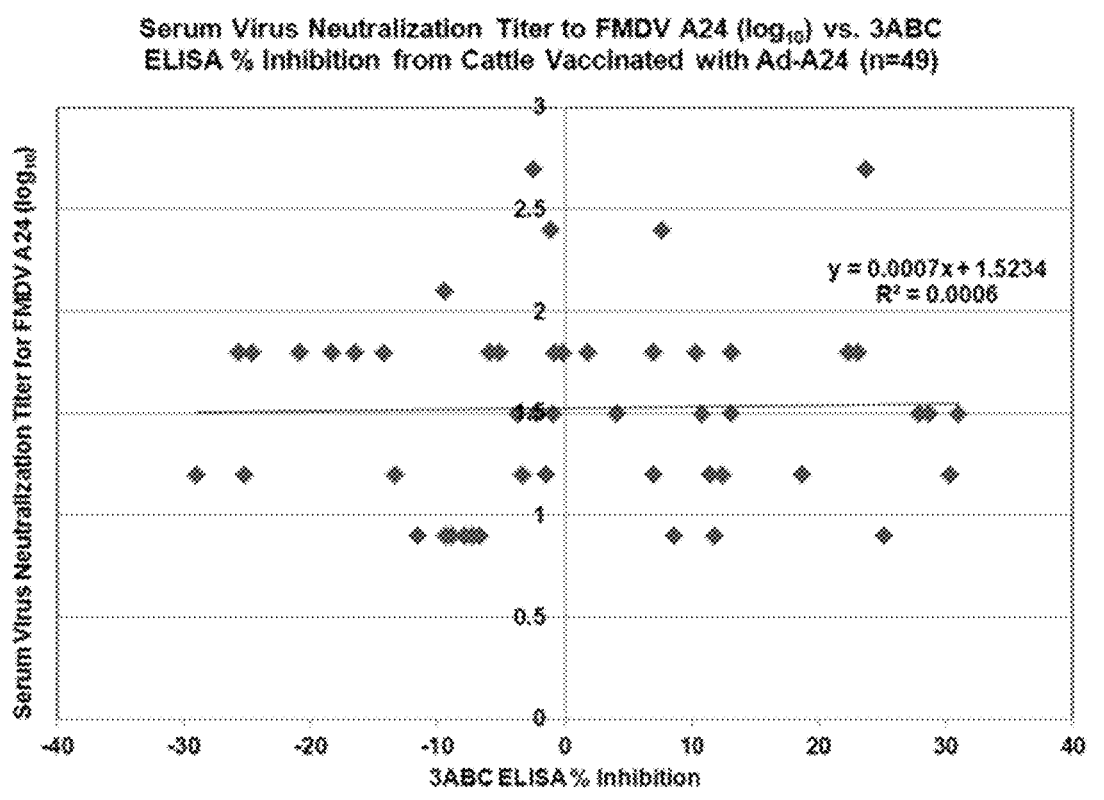

Cattle from Michigan and Nebraska were vaccinated with the conditionally licensed Ad-A24 FMD vaccine (USDA product code 1FM1.R0). Forty-nine cattle serum samples collected approximately 11 months post-vaccination were positive using serum virus neutralization (SVN) to detect antibodies produced to the FMDV A24 capsid proteins (average titer=1.5 log 10, std. dev.=0.5, range 0.9 to 2.7 log 10) (FIG. 12). Antibodies were not detected to the FMDV non-structural proteins, as expected, since these animals had been vaccinated but not infected with FMDV. In the 3ABC ELISA, the average % inhibition was 1.5%, std. dev.=16%, and range=−29% to 31%. There was no correlation between the SVN titers to the A24 antigen and the percent inhibition measured in the 3ABC ELISA; correlation=0.025 ($R^2$=0.0006). This data indicates that the 3ABC ELISA is suitable as a companion diagnostic assay for AdFMD based vaccines.

Example: Diagnostic Sensitivity Evaluation

Positive Reference Sample Set (Known Positive Status) Analysis

Serum samples obtained from 139 animals, at least 10 to 14 days post-infection with a known serotype of FMDV, were evaluated for their response in the 3ABC ELISA and with the commercially available PrioCHECK® FMDV NS Antibody ELISA. The samples were obtained from 112 cattle, 18 pigs, 5 sheep, and 4 goats that were experimentally infected with one of the seven FMDV serotypes; this sample set covered the full spectrum of all seven serotypes. All 139 serum samples were positive with the FMDV 3ABC ELISA assay, and 136 of those samples were positive with the PrioCHECK® FMDV NS Antibody ELISA (Table 9). The results demonstrate that the 3ABC ELISA can detect antibodies produced to the seven serotypes of FMDV 3ABC nonstructural protein in diverse animal species.

Figure 13:
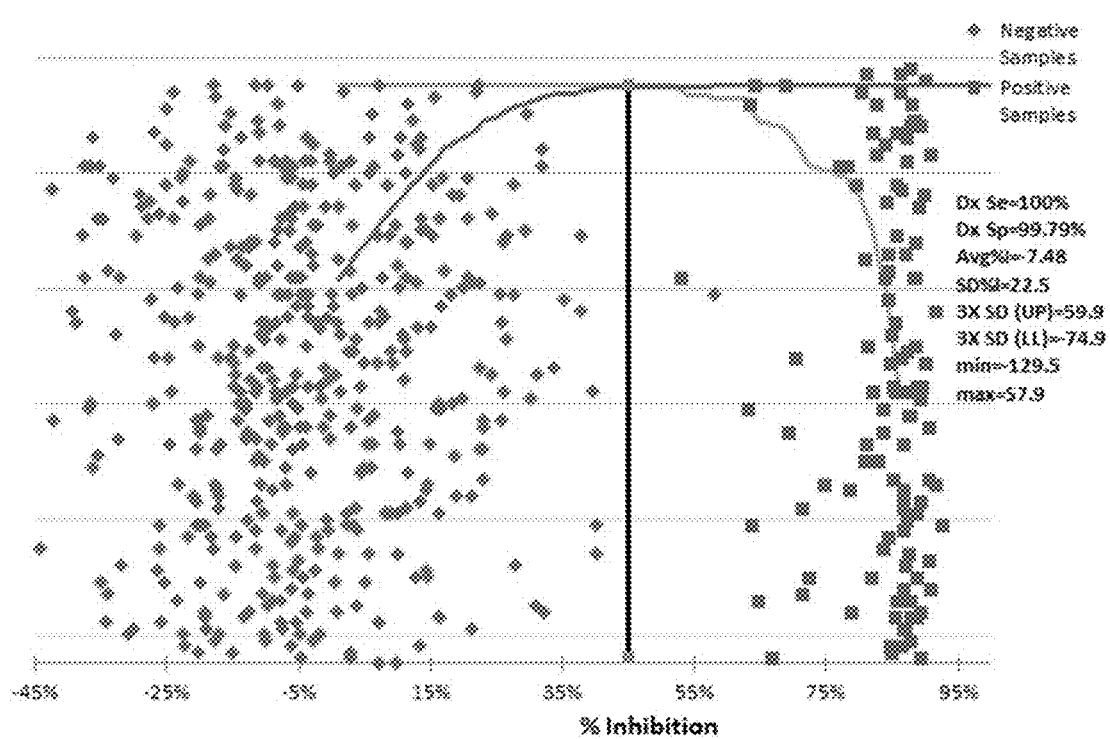
FIG. 13 shows percent inhibition (% I) distribution of 486 bovine FMDV negative and 139 FMDV positive samples. The vertical line denotes the 45% I cut-off; Dx Se denotes diagnostic sensitivity; Dx Sp denotes specificity.

The diagnostic sensitivity was calculated using the results from the 139 serum samples (Table 10). Since all 139 serum samples that were collected from FMDV-infected animals (known positives) exhibited a positive response in the 3ABC ELISA, the diagnostic sensitivity was 100%. In the Prio-CHECK® FMDV NS Antibody ELISA, 136 of the same 139 samples were positive, which indicates a diagnostic sensitivity of 97.8%. The % inhibition (% I) distribution of these samples in the 3ABC ELISA are provided graphically on the right side of the vertical line in FIG. 13.

TABLE 9

Detection of antibodies to FMDV produced in animals infected with one of seven serotypes of FMDV

| FMDV Serotype* | 3ABC ELISA Positive | FMDV PrioCHECK ® Positive |
|---|---|---|
| A | 52 | 52 |
| O | 23 | 23 |
| C | 1 | 1 |
| SAT1 | 22 | 20 |
| SAT2 | 3 | 3 |
| SAT3 | 20 | 20 |
| Asia-1 | 18 | 17 |
| Total | 139 | 136 |

*Serum samples were from 112 bovine, 18 swine, 5 ovine, and 4 caprine experimentally infected animals.

TABLE 10

Diagnostic sensitivity of the 3ABC ELISA compared to the PrioCHECK with reference to samples that were obtained from animals infected with FMDV.

| Assay Result | 3ABC ELISA | FMDV PrioCHECK |
|---|---|---|
| Positive | 139 | 136 |
| Negative | 0 | 3 |
| Total Samples Tested (Known Positives) | 139 | 139 |
| Diagnostic Sensitivity | 100% | 97.8% |

Diagnostic Specificity Evaluation

Figure 14:
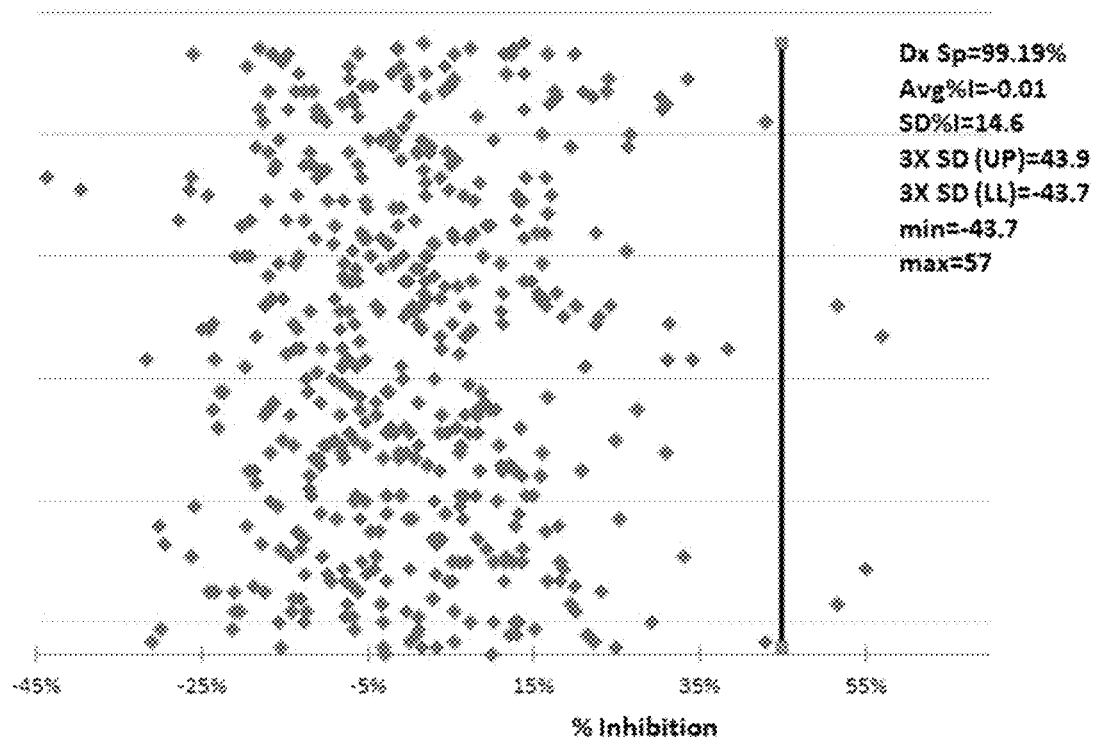
FIG. 14 shows percent inhibition (% I) distribution of 491 bovine negative samples. The vertical line denotes the 45% I cut-off; Dx Sp denotes diagnostic specificity.

Approximately 500 bovine sera were split into two sample sets and tested by two laboratories, to assessed diagnostic specificity. At TVMDL, there were 4 false positives out of 491 serum samples using 45% inhibition cut-off, resulting in 99.2% diagnostic specificity (FIG. 14). At FADDL, one false positive (out of 486) was obtained, resulting in 99.8% diagnostic specificity; this one false positive was one of the four false positives identified at TVMDL, i.e., same biological sample. Comparison of the TVMDL and FADDL % inhibition for the samples resulted in TVMDL % I average (Avg)=−0.018, standard deviation (SD)=14.6; FADDL % I Avg=−7.48, SD=22.5; p value <0.05. Although a significant difference in % I was observed, equivalent diagnostic specificity (probability that a negative sample test negative) was obtained; TVMDL Dx sp=99.2% and FADDL Dx sp=99.8%. This indicates that the assay of the current disclosure exhibits a wide % I distribution range for negatives (see FIGS. 12, 13, and 14) enabling tolerance of % I differences between labs and testers and high diagnostic specificity.

Furthermore, 200 samples from this 491 sample set was also tested with the PrioCHECK® FMDV NS Antibody ELISA at FADDL and 8 false positives were identified, resulting in 96% diagnostic specificity; only one of the false positives corresponded to the 3ABC ELISA false positive identified by TVMDL, i.e., same biological sample.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. An isolated monoclonal antibody or antigen binding fragment thereof, wherein the monoclonal antibody is Mab 40C8 as produced by the hybridoma which is deposited with the American Type Culture Collection with Designation PTA-122531.

2. The monoclonal antibody or antigen binding fragment thereof of claim 1, wherein the monoclonal antibody or antigen binding fragment thereof is conjugated to a label.

3. The monoclonal antibody of claim 2, wherein the label is selected from an enzyme label, a radioisotope, a fluorescent label, or a bioluminescent label.

4. A method of detecting FMDV infection in an animal, the method comprising contacting a sample from a animal with an monoclonal antibody or antigen binding fragment according to claim 1 that specifically binds to the 3ABC non-structural protein of FMDV.

5. The method of claim 4, wherein the sample obtained from the animal is a body-fluid sample or a tissue sample.

6. The method of claim 5, wherein the body-fluid sample is aqueous humor, vitreous humor, blood serum, blood plasma, cerebrospinal fluid, endolymph, perilymph, exudates, lymph, mucus, pericardial fluid, pleural fluid, synovial fluid, milk, or oral fluids.

7. The method of claim 5, wherein the tissue sample is brain, eyes, pineal gland, pituitary gland, thyroid gland, parathyroid glands, thorax, heart, lungs, esophagus, thymus gland, pleura, adrenal glands, appendix, gall blader, urinary blader, large intestine, small intestine, kidneys, liver, pancreas, spleen, stoma, prostate gland, testes, ovaries, or uterus.

8. The method of claim 4, wherein the assay is a Western blot analysis.

9. The method of claim 4, wherein the assay is an ELISA.

10. The method of claim 9, wherein the ELISA is sandwich ELISA, or competitive ELISA.

11. The method of claim 10, wherein the competitive ELISA is performed using an immunoassay plate, wherein the immunoassay plate is coated with one or more polypeptide consisting essentially of an amino acid sequence selected from SEQ ID NO: 2, SEQ ID NO: 3, SEQ ID NO: 4, SEQ ID NO: 5, SEQ ID NO: 6, or SEQ ID NO: 12.

12. The method of claim 9, wherein the monoclonal antibody or antigen binding fragment thereof is conjugated to an enzyme.

13. The method of claim 12, wherein the enzyme is horseradish peroxidase.

14. The method of claim 4, wherein the monoclonal antibody or antigen binding fragment thereof is conjugated to a label.

15. The method of claim 14, wherein the label is an enzyme label, a radioisotope, a fluorescent label, or a bioluminescent label.

16. A kit comprising a monoclonal antibody or antigen binding fragment according to claim 1.

17. The kit of claim 16, wherein said kit further comprises an immunoassay plate coated with a polypeptide comprising the amino acid sequence selected from SEQ ID NO: 2, SEQ ID NO: 3, SEQ ID NO: 4, SEQ ID NO: 5, SEQ ID NO: 6 or SEQ ID NO: 12, FMDV non-structural protein 3ABC or combinations thereof.

18. The kit of claim 16, wherein the monoclonal antibody or antigen binding fragment thereof is conjugated to a label.

19. The kit of claim 16, wherein said label is an enzyme label, a radioisotope, a fluorescent label, or a bioluminescent label.

* * * * *

SEQUENCE LISTING

<160> NUMBER OF SEQ ID NOS: 30

<210> SEQ ID NO 1
<211> LENGTH: 437
<212> TYPE: PRT
<213> ORGANISM: Foot-and-mouth disease virus
<220> FEATURE:
<221> NAME/KEY: MISC_FEATURE
<222> LOCATION: (1)..(437)
<223> OTHER INFORMATION: 3ABC protein from FMDV Campos 437 (GenBank: CAC86575.1, amino acids 1426-1862)

<400> SEQUENCE: 1

Ile Ser Ile Pro Ser Gln Lys Ser Val Leu Tyr Phe Leu Ile Glu Lys
1               5                   10                  15

Gly Gln His Glu Ala Ala Ile Glu Phe Phe Glu Gly Met Val His Asp
            20                  25                  30

Ser Ile Lys Glu Glu Leu Arg Pro Leu Ile Gln Gln Thr Ser Phe Val
        35                  40                  45

Lys Arg Ala Phe Lys Arg Leu Lys Glu Asn Phe Glu Ile Val Ala Leu
    50                  55                  60

Cys Leu Thr Leu Leu Ala Asn Ile Val Ile Met Ile Arg Glu Thr Arg
65                  70                  75                  80

Lys Arg Gln Lys Met Val Asp Ala Val Asn Glu Tyr Ile Glu Lys
                85                  90                  95

Ala Asn Ile Thr Thr Asp Asp Lys Thr Leu Asp Glu Ala Glu Lys Ser
            100                 105                 110

Pro Leu Glu Thr Ser Gly Ala Ser Thr Val Gly Phe Arg Glu Arg Thr
        115                 120                 125

Leu Pro Gly Gln Lys Ala Cys Asp Asp Val Asn Ser Glu Pro Ala Gln
130                 135                 140

Pro Val Glu Glu Gln Pro Gln Ala Glu Gly Pro Tyr Ala Gly Pro Leu
145                 150                 155                 160

Glu Arg Gln Lys Pro Leu Lys Val Arg Ala Lys Leu Pro Gln Gln Glu
                165                 170                 175

Gly Pro Tyr Ala Gly Pro Met Glu Arg Gln Lys Pro Leu Lys Val Lys
            180                 185                 190

Ala Lys Ala Pro Val Val Lys Glu Gly Pro Tyr Glu Gly Pro Val Lys
        195                 200                 205

Lys Pro Val Ala Leu Lys Val Lys Ala Lys Asn Leu Ile Val Thr Glu
210                 215                 220

Ser Gly Ala Pro Pro Thr Asp Leu Gln Lys Met Val Met Gly Asn Thr
225                 230                 235                 240

Lys Pro Val Glu Leu Ile Leu Asp Gly Lys Thr Val Ala Ile Cys Cys
                245                 250                 255

Ala Thr Gly Val Phe Gly Thr Ala Tyr Leu Val Pro Arg His Leu Phe
            260                 265                 270

Ala Glu Lys Tyr Asp Lys Ile Met Leu Asp Gly Arg Ala Met Thr Asp
        275                 280                 285

Ser Asp Tyr Arg Val Phe Glu Phe Glu Ile Lys Val Lys Gly Gln Asp
290                 295                 300

Met Leu Ser Asp Ala Ala Leu Met Val Leu His Arg Gly Asn Arg Val
305                 310                 315                 320

Arg Asp Ile Thr Lys His Phe Arg Asp Thr Ala Arg Met Lys Lys Gly
                325                 330                 335

Thr Pro Val Val Gly Val Ile Asn Asn Ala Asp Val Gly Arg Leu Ile
            340                 345                 350

Phe Ser Gly Glu Ala Leu Thr Tyr Lys Asp Ile Val Val Cys Met Asp
        355                 360                 365

Gly Asp Thr Met Pro Gly Leu Phe Ala Tyr Arg Ala Ala Thr Lys Ala
370                 375                 380

Gly Tyr Cys Gly Gly Ala Val Leu Ala Lys Asp Gly Ala Asp Thr Phe
385                 390                 395                 400

Ile Val Gly Thr His Ser Ala Gly Gly Asn Gly Val Gly Tyr Cys Ser
                405                 410                 415

Cys Val Ser Arg Ser Met Leu Leu Lys Met Lys Ala His Ile Asp Pro
            420                 425                 430

Glu Pro His His Glu
        435

<210> SEQ ID NO 2
<211> LENGTH: 209
<212> TYPE: PRT
<213> ORGANISM: Artificial Sequence
<220> FEATURE:
<223> OTHER INFORMATION: FMDV sequence encoded by pET31b+12X3B

<400> SEQUENCE: 2

```
Gly Gly Gly Gly Ser Pro Tyr Val Gly Pro Leu Glu Arg Gln Lys Pro
1               5                   10                  15

Leu Gly Gly Gly Ser Pro Tyr Ser Gly Pro Leu Glu Arg Gln Lys
            20              25                  30

Pro Leu Gly Gly Gly Ser Pro Tyr Gly Gly Pro Leu Glu Arg Gln
                35                  40                  45

Lys Pro Leu Gly Gly Gly Ser Pro Tyr Ala Gly Pro Val Glu Arg
        50                  55                  60

Gln Lys Pro Leu Gly Gly Gly Ser Pro Tyr Ala Gly Pro Met Glu
65                      70                  75              80

Arg Gln Lys Pro Leu Gly Gly Gly Ser Pro Tyr Thr Gly Pro Leu
                85                      90                  95

Glu Arg Gln Arg Pro Leu Gly Gly Gly Ser Pro Tyr Ala Gly Pro
            100                 105                 110

Leu Glu Arg Gln Gln Pro Leu Gly Gly Gly Ser Pro Tyr Thr Gly
            115                 120                 125

Pro Leu Glu Arg Gln Lys Pro Leu Gly Gly Gly Ser Pro Tyr Ala
        130                 135             140

Gly Pro Leu Glu Arg Gln Arg Pro Leu Gly Gly Gly Ser Pro Tyr
145                 150                 155                 160

Ala Gly Pro Leu Glu Arg Gln Lys Pro Leu Gly Gly Gly Ser Pro
            165                 170                 175

Tyr Ala Gly Pro Leu Glu Arg Gln Ile Pro Leu Gly Gly Gly Ser
            180                 185                 190

Pro Tyr Ala Gly Ala Phe Glu Arg Gln Lys Thr Leu Gly Gly Gly
        195                 200                 205

Ser

<210> SEQ ID NO 3
<211> LENGTH: 14
<212> TYPE: PRT
<213> ORGANISM: Artificial Sequence
<220> FEATURE:
<223> OTHER INFORMATION: Sequence of the epitope for Mab 40C8 binding

<400> SEQUENCE: 3

Gly Pro Tyr Ala Gly Pro Leu Glu Arg Gln Lys Pro Leu Lys
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Sequence of the minimal epitope for Mab 40C8
      binding

<400> SEQUENCE: 4

Gly Pro Leu Glu Arg Gln
1               5

<210> SEQ ID NO 5
<211> LENGTH: 6
<212> TYPE: PRT
<213> ORGANISM: Artificial Sequence
<220> FEATURE:
<223> OTHER INFORMATION: Alternate sequence of the minimal epitopes for
      MAB 40C8
<220> FEATURE:
<221> NAME/KEY: MISC_FEATURE
```

```
<222> LOCATION: (2)..(3)
<223> OTHER INFORMATION: Xaa is any amino acid

<400> SEQUENCE: 5

Gly Xaa Xaa Glu Arg Gln
1 5

<210> SEQ ID NO 6
<211> LENGTH: 15
<212> TYPE: PRT
<213> ORGANISM: Artificial Sequence
<220> FEATURE:
<223> OTHER INFORMATION: FMDV peptide

<400> SEQUENCE: 6

Cys Gly Pro Tyr Ala Gly Pro Leu Glu Arg Gln Lys Pro Leu Lys
1 5 10 15

<210> SEQ ID NO 7
<211> LENGTH: 20
<212> TYPE: DNA
<213> ORGANISM: Artificial Sequence
<220> FEATURE:
<223> OTHER INFORMATION: Forward PCR primer
<400> SEQUENCE: 7
caattccttc ccaaaaatct 20

<210> SEQ ID NO 8
<211> LENGTH: 21
<212> TYPE: DNA
<213> ORGANISM: Artificial Sequence
<220> FEATURE:
<223> OTHER INFORMATION: Reverse PCR primer
<400> SEQUENCE: 8
gtggtgtggt tcggggtcca a 21

<210> SEQ ID NO 9
<211> LENGTH: 6708
<212> TYPE: DNA
<213> ORGANISM: Artificial Sequence
<220> FEATURE:
<223> OTHER INFORMATION: Nucleotide sequence of plasmid pET30c O1C 3ABC*

<400> SEQUENCE: 9
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300
ctttaatagt ggactcttgt tccaaactgg aacaacactc aaccctatct cggtctattc 360
ttttgattta taagggattt tgccgatttc ggcctattgg ttaaaaaatg agctgattta 420
acaaaaattt aacgcgaatt ttaacaaaat attaacgttt acaatttcag gtggcacttt 480
tcggggaaat gtgcgcggaa cccctatttg tttatttttc taaatacatt caaatatgta 540
tccgctcatg aattaattct tagaaaaact catcgagcat caaatgaaac tgcaatttat 600
tcatatcagg attatcaata ccatattttt gaaaaagccg tttctgtaat gaaggagaaa 660
actcaccgag gcagttccat aggatggcaa gatcctggta tcggtctgcg attccgactc 720

```
gtccaacatc aataacaacct attaatttcc cctcgtcaaa aataaggtta tcaagtgaga    780
aatcaccatg agtgacgact gaatccggtg agaatggcaa aagtttatgc atttcttcc     840 agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg caacgctac    1200 ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc    1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980 ccaggggaa acgcctggta tctttatagt cctgtcgggt ttcgccacct ctgacttgag    2040
cgtcgatttt tgtgatgctc gtcagggggg cggagcctat ggaaaaacgc cagcaacgcg   2100 gccttttac ggttcctggc cttttgctgg cctttgctc acatgttctt tcctgcgtta     2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
```

```
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatgtcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccgaaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920 gcgcggtga tgcggccac gatgcgtccg gcgtagagga tcgagatcga tctcgatccc    4980
gcgaaattaa tacgactcac tatagggaa ttgtgagcgg ataacaattc ccctctagaa    5040
ataattttgt ttaactttaa gaaggagata tacatatgca ccatcatcat catcattctt    5100
ctggtctggt gccacgcggt tctggtatga agaaaccgc tgctgctaaa ttcgaacgcc    5160
agcacatgga cagcccagat ctgggtaccg acgacgacga caaggccatg ggatatctgt    5220
ggatcccaat tccttcccaa aaatctgtgt tgtactttct cattgagaag gccaacatg    5280 aggcagcaat tgaattcttt gagggcatgg tccacgactc catcaaagag gaactccgac    5340
ccctcatcca acaaacttca tttgtgaaac gcgctttcaa gcgcctgaag gaaaattttg    5400
agattgttgc tctgtgttta acacttttgg caaacattgt gatcatgatc cgtgagactc    5460
```

```
gcaagaggca gaaatggtg gatgatgcag tgaatgagta cattgagaaa gcaaacatca    5520
ccacagatga caagactctt gacgaggcgg agaagagccc tctagagacc agcggcgcca    5580
gcaccgttgg ctttagagag agaactctcc caggtcaaaa ggcatgcgat gacgtgaact    5640
ccgagcctgc ccaacctgtt gaggagcaac acaagctga aggacccta gccggaccac    5700 tcgagcgtca gaaacctctg aaagtgagag ccaagctccc acagcaggag gggccttacg    5760
ctggtccgat ggagagacag aaaccgctaa aagtgaaagc aaaagccccg gtcgtgaagg    5820
aaggacctta cgagggaccg gtgaagaagc ctgtcgcttt gaaagtgaaa gctaagaacc    5880
tgattgtcac tgagagtggt gctccaccga ccgacttgca aaagatggtc atgggcaaca    5940
caaagcctgt tgagctcatc ctcgacggga agacagtagc catctgctgc gctactggag    6000
tgtttggcac tgcttacctc gtgcctcgtc acctcttcgc agagaagtat gacaagatca    6060
tgttggacgg cagagccatg acagacagtg actacagagt gtttgagttt gagatcaaag    6120
taaaaggaca ggacatgctc tcagacgccg cgctcatggt gctccaccgt gggaaccgcg    6180
tgagggacat cacgaagcac tttcgtgaca cagcaagaat gaagaaaggc acccccgttg    6240
tcggtgtgat caacaacgcc gatgtcggga gactgatttt ctctggtgag gcccttactt    6300
acaaggacat tgtggtttgc atggacggag acaccatgcc tggcctcttt gcctacagag    6360
ccgccaccaa ggctggttat cgtggaggag ccgtcctcgc taaggacggg gctgacacgt    6420
tcatcgttgg cacccactcc gctggaggca agggagttgg atactgctca tgcgtttcca    6480
ggtccatgct tcttaaaatg aaggcacaca ttgaccccga accacaccac aagcttgcgg    6540
ccgcactcga gcaccaccac caccaccact gagatccggc tgctaacaaa gcccgaaagg    6600
aagctgagtt ggctgctgcc accgctgagc aataactagc ataaccccctt ggggcctcta    6660 aacgggtctt gaggggtttt ttgctgaaag gaggaactat atccggat                6708
```

<210> SEQ ID NO 10
<211> LENGTH: 1304
<212> TYPE: DNA
<213> ORGANISM: Artificial Sequence
<220> FEATURE:
<223> OTHER INFORMATION: Nucleotide sequence encoding O1C 3ABC*

<400> SEQUENCE: 10

```
caattccttc ccaaaaatct gtgttgtact ttctcattga aagggccaa catgaggcag      60 caattgaatt ctttgagggc atggtccacg actccatcaa agaggaactc cgaccccctca    120 tccaacaaac ttcatttgtg aaacgcgctt tcaagcgcct gaaggaaaat tttgagattg    180
ttgctctgtg tttaacactt ttggcaaaca ttgtgatcat gatccgtgag actcgcaaga    240
ggcagaaaat ggtggatgat gcagtgaatg agtacattga aaagcaaac atcaccacag    300 atgacaagac tcttgacgag gcggagaaga gccctctaga ccagcggc gccagcaccg    360 ttggctttag agagaaact ctcccaggtc aaaaggcatg cgatgacgtg aactccgagc    420
ctgcccaacc tgttgaggag caaccacaag ctgaaggacc ctacgccgga ccactcgagc    480
gtcagaaacc tctgaaagtg agagccaagc tcccacagca ggaggggcct tacgctggtc    540
cgatggagag acagaaaccg ctaaaagtga agcaaaagc cccggtcgtg aaggaaggac    600
cttacgaggg accggtgaag aagcctgtcg ctttgaaagt gaaagctaag aacctgattg    660
tcactgagag tggtgctcca ccgaccgact tgcaaaagat ggtcatgggc aacacaaagc    720
ctgttgagct catcctcgac gggaagacag tagccatctg ctgcgctact ggagtgtttg    780
gcactgctta cctcgtgcct cgtcacctct tcgcagagaa gtatgacaag atcatgttgg    840
```

-continued

```
acggcagagc catgacagac agtgactaca gagtgtttga gtttgagatc aaagtaaaag    900
gacaggacat gctctcagac gccgcgctca tggtgctcca ccgtgggaac cgcgtgaggg    960
acatcacgaa gcactttcgt gacacagcaa gaatgaagaa aggcaccccc gttgtcggtg   1020
tgatcaacaa cgccgatgtc gggagactga ttttctctgg tgaggccctt acttacaagg   1080
acattgtggt ttgcatggac ggagacacca tgcctggcct ctttgcctac agagccgcca   1140
ccaaggctgg ttatcgtgga ggagccgtcc tcgctaagga cggggctgac acgttcatcg   1200
ttggcaccca ctccgctgga ggcaagggag ttggataccg ctcatgcgtt ccaggtccaa   1260
tgcttcttaa aatgaaggca cacattgacc ccgaaccaca ccac                    1304
```

<210> SEQ ID NO 11
<211> LENGTH: 447
<212> TYPE: PRT
<213> ORGANISM: Artificial Sequence
<220> FEATURE:
<223> OTHER INFORMATION: Amino acid sequence corresponding to the
      serotype O FMDV 3ABC* protein and encoding a His6 tag for E. coli
      expression

<400> SEQUENCE: 11

```
Ile Pro Ser Gln Lys Ser Val Leu Tyr Phe Leu Ile Glu Lys Gly Gln
1               5                   10                  15

His Glu Ala Ala Ile Glu Phe Phe Glu Gly Met Val His Asp Ser Ile
            20                  25                  30

Lys Glu Glu Leu Arg Pro Leu Ile Gln Gln Thr Ser Phe Val Lys Arg
        35                  40                  45

Ala Phe Lys Arg Leu Lys Glu Asn Phe Glu Ile Val Ala Leu Cys Leu
    50                  55                  60

Thr Leu Leu Ala Asn Ile Val Ile Met Ile Arg Glu Thr Arg Lys Arg
65                  70                  75                  80

Gln Lys Met Val Asp Asp Ala Val Asn Glu Tyr Ile Glu Lys Ala Asn
                85                  90                  95

Ile Thr Thr Asp Asp Lys Thr Leu Asp Glu Ala Glu Lys Ser Pro Leu
            100                 105                 110

Glu Thr Ser Gly Ala Ser Thr Val Gly Phe Arg Glu Arg Thr Leu Pro
        115                 120                 125

Gly Gln Lys Ala Cys Asp Asp Val Asn Ser Glu Pro Ala Gln Pro Val
    130                 135                 140

Glu Glu Gln Pro Gln Ala Glu Gly Pro Tyr Ala Gly Pro Leu Glu Arg
145                 150                 155                 160

Gln Lys Pro Leu Lys Val Arg Ala Lys Leu Pro Gln Gln Glu Gly Pro
                165                 170                 175

Tyr Ala Gly Pro Met Glu Arg Gln Lys Pro Leu Lys Val Lys Ala Lys
            180                 185                 190

Ala Pro Val Val Lys Glu Gly Pro Tyr Glu Gly Pro Val Lys Lys Pro
        195                 200                 205

Val Ala Leu Lys Val Lys Ala Lys Asn Leu Ile Val Thr Glu Ser Gly
    210                 215                 220

Ala Pro Pro Thr Asp Leu Gln Lys Met Val Met Gly Asn Thr Lys Pro
225                 230                 235                 240

Val Glu Leu Ile Leu Asp Gly Lys Thr Val Ala Ile Cys Cys Ala Thr
                245                 250                 255

Gly Val Phe Gly Thr Ala Tyr Leu Val Pro Arg His Leu Phe Ala Glu
            260                 265                 270
```

```
Lys Tyr Asp Lys Ile Met Leu Asp Gly Arg Ala Met Thr Asp Ser Asp
            275                 280                 285

Tyr Arg Val Phe Glu Phe Glu Ile Lys Val Lys Gly Gln Asp Met Leu
290                 295                 300

Ser Asp Ala Ala Leu Met Val Leu His Arg Gly Asn Arg Val Arg Asp
305                 310                 315                 320

Ile Thr Lys His Phe Arg Asp Thr Ala Arg Met Lys Lys Gly Thr Pro
                325                 330                 335

Val Val Gly Val Ile Asn Asn Ala Asp Val Gly Arg Leu Ile Phe Ser
                340                 345                 350

Gly Glu Ala Leu Thr Tyr Lys Asp Ile Val Val Cys Met

<213> ORGANISM: Artificial Sequence
<220> FEATURE:
<223> OTHER INFORMATION: 3 ABC peptide

<400> SEQUENCE: 15

Gly Pro Tyr Ala Gly Pro Leu Glu Arg Gln Arg Pro Leu Lys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: 3 ABC peptide

<400> SEQUENCE: 16

Gly Pro Tyr Ala Gly Pro Leu Glu Arg Gln Gln Pro Leu Lys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: 3 ABC peptide

<400> SEQUENCE: 17

Gly Pro Tyr Thr Gly Pro Leu Glu Arg Gln Arg Pro Leu Lys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: 3 ABC peptide

<400> SEQUENCE: 18

Gly Pro Tyr Ala Gly Pro Met Glu Arg Gln Lys Pro Leu Lys
1               5                   10

<210> SEQ ID NO 19
<211> LENGTH: 14
<212> TYPE: PRT
<213> ORGANISM: Artificial Sequence
<220> FEATURE:
<223> OTHER INFORMATION: 3 ABC peptide

<400> SEQUENCE: 19

Gly Pro Tyr Val Gly Pro Leu Glu Arg Gln Lys Pro Leu Lys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: 3 ABC peptide

<400> SEQUENCE: 20

Gly Pro Tyr Ser Gly Pro Leu Glu Arg Gln Lys Pro Leu Lys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: 3 ABC peptide

<400> SEQUENCE: 21

Gly Pro Tyr Gly Gly Pro Leu Glu Arg Gln Lys Pro Leu Lys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: 3 ABC peptide

<400> SEQUENCE: 22

Gly Pro Tyr Ala Gly Pro Val Glu Arg Gln Lys Pro Leu Arg
1               5                   10

<210> SEQ ID NO 23
<211> LENGTH: 14
<212> TYPE: PRT
<213> ORGANISM: Artificial Sequence
<220> FEATURE:
<223> OTHER INFORMATION: 3 ABC peptide

<400> SEQUENCE: 23

Gly Pro Tyr Ala Gly Pro Leu Glu Arg Gln Lys Pro Leu Thr
1               5                   10

<210> SEQ ID NO 24
<211> LENGTH: 14
<212> TYPE: PRT
<213> ORGANISM: Artificial Sequence
<220> FEATURE:
<223> OTHER INFORMATION: 3 ABC peptide

<400> SEQUENCE: 24

Gly Pro Tyr Ala Gly Pro Leu Glu Arg Gln Lys Pro Leu Arg
1               5                   10

<210> SEQ ID NO 25
<211> LENGTH: 14
<212> TYPE: PRT
<213> ORGANISM: Artificial Sequence
<220> FEATURE:
<223> OTHER INFORMATION: 3 ABC peptide

<400> SEQUENCE: 25

Gly Pro Tyr Ala Gly Pro Leu Glu Arg Gln Lys Pro Leu Gln
1               5                   10

<210> SEQ ID NO 26
<211> LENGTH: 14
<212> TYPE: PRT
<213> ORGANISM: Artificial Sequence
<220> FEATURE:
<223> OTHER INFORMATION: 3 ABC peptide

<400> SEQUENCE: 26

Gly Pro Tyr Ala Gly Pro Leu Glu Arg Gln Lys Pro Leu Glu
1               5                   10

<210> SEQ ID NO 27
<211> LENGTH: 14
<212> TYPE: PRT
<213> ORGANISM: Artificial Sequence
<220> FEATURE:

```
<223> OTHER INFORMATION: 3 ABC peptide

<400> SEQUENCE: 27

Gly Pro Tyr Ala Gly Pro Leu Glu Arg Gln Ile Pro Leu Lys
1               5                   10

<210> SEQ ID NO 28
<211> LENGTH: 14
<212> TYPE: PRT
<213> ORGANISM: Artificial Sequence
<220> FEATURE:
<223> OTHER INFORMATION: 3 ABC peptide

<400> SEQUENCE: 28

Gly Pro Tyr Ala Gly Ala Phe Glu Arg Gln Lys Thr Leu Lys
1               5                   10

<210> SEQ ID NO 29
<211> LENGTH: 8
<212> TYPE: PRT
<213> ORGANISM: Artificial Sequence
<220> FEATURE:
<223> OTHER INFORMATION: synthetic

<400> SEQUENCE: 29

Ile Pro Ile Pro Ser Gln Lys Ser
1               5

<210> SEQ ID NO 30
<211> LENGTH: 5
<212> TYPE: PRT
<213> ORGANISM: Artificial Sequence
<220> FEATURE:
<223> OTHER INFORMATION: synthetic

<400> SEQUENCE: 30

Pro Glu Pro His His
1               5
```